US012740940B2

(12) United States Patent
Raju

(10) Patent No.: US 12,740,940 B2
(45) Date of Patent: Sep. 22, 2026

(54) TREATMENT OF LOW-GRADE INTERMEDIATE-RISK NON-MUSCLE-INVASIVE BLADDER CANCER WITH A THERMALLY GELLING PHARMACEUTICAL COMPOSITION CONTAINING MITOMYCIN

(71) Applicant: UROGEN PHARMA LTD., Ra'anana (IL)

(72) Inventor: Sunil Raju, Princeton, NJ (US)

(73) Assignee: UROGEN PHARMA LTD., Ra'anana (IL)

( * ) Notice: Subject to any disclaimer, the term of this patent is extended or adjusted under 35 U.S.C. 154(b) by 0 days.

(21) Appl. No.: 18/784,354

(22) Filed: Jul. 25, 2024

(65) Prior Publication Data

US 2025/0032409 A1 Jan. 30, 2025

Related U.S. Application Data

(60) Provisional application No. 63/640,252, filed on Apr. 30, 2024, provisional application No. 63/515,352, filed on Jul. 25, 2023.

(51) Int. Cl.

| | |
|---|---|
| ***A61K 9/06*** | (2006.01) |
| ***A61K 31/407*** | (2006.01) |
| ***A61K 47/10*** | (2017.01) |
| ***A61K 47/38*** | (2006.01) |
| ***A61P 35/00*** | (2006.01) |

(52) U.S. Cl.

CPC .............. *A61K 9/06* (2013.01); *A61K 31/407* (2013.01); *A61K 47/10* (2013.01); *A61K 47/38* (2013.01); *A61P 35/00* (2018.01)

(58) Field of Classification Search

CPC ........ A61K 9/06; A61K 31/407; A61K 47/10; A61K 47/38; A61P 35/00; A61P 13/10

See application file for complete search history.

(56) References Cited

U.S. PATENT DOCUMENTS

| | | | |
|---|---|---|---|
| 6,286,513 | B1 | 9/2001 | Au et al. |
| 6,482,435 | B1 | 11/2002 | Stratton et al. |
| 9,040,074 | B2 | 5/2015 | Holzer et al. |
| 9,801,854 | B1 | 10/2017 | Strauss-Ayali et al. |
| 9,950,069 | B2 | 4/2018 | Holzer et al. |
| 10,039,832 | B2 | 8/2018 | Holzer et al. |
| 10,471,150 | B2 | 11/2019 | Konorty et al. |
| 2004/0009212 | A1 | 1/2004 | Tsai |
| 2007/0275110 | A1 | 11/2007 | Dott et al. |
| 2009/0142259 | A1 | 6/2009 | Gao et al. |
| 2009/0214685 | A1 | 8/2009 | Hunt |
| 2010/0015200 | A1 | 1/2010 | McClain et al. |
| 2013/0046275 | A1 | 2/2013 | Holzer et al. |
| 2014/0105884 | A1 | 4/2014 | Konorty et al. |
| 2014/0142191 | A1 | 5/2014 | De La Zerda et al. |
| 2015/0366974 | A1 | 12/2015 | Holzer et al. |
| 2016/0256391 | A1 | 9/2016 | Schuldt-Lieb et al. |
| 2017/0112935 | A1 | 4/2017 | Holzer et al. |
| 2017/0128424 | A1 | 5/2017 | Rothstein |
| 2017/0136127 | A1 | 5/2017 | Maki et al. |
| 2017/0143833 | A1 | 5/2017 | De La Zerda et al. |
| 2019/0201334 | A1 | 7/2019 | Hakim et al. |
| 2020/0114008 | A1 | 4/2020 | Konorty |
| 2022/0118096 | A1 | 4/2022 | Konorty |
| 2022/0202773 | A1 | 6/2022 | Hionidi et al. |
| 2023/0233685 | A1 | 7/2023 | Holzer et al. |
| 2023/0241220 | A1 | 8/2023 | Holzer et al. |
| 2023/0241221 | A1 | 8/2023 | Holzer et al. |

FOREIGN PATENT DOCUMENTS

| | | | |
|---|---|---|---|
| EP | 0386960 | A2 | 9/1990 |
| WO | 2011/089604 | A2 | 7/2011 |
| WO | 2013/011504 | A1 | 1/2013 |
| WO | 2018/169960 | A1 | 9/2018 |
| WO | 2022/123480 | A1 | 6/2022 |

OTHER PUBLICATIONS

Kokorovic, UGN-101, Ther Adv Med Oncol, p. 1 Jul. 2020.*
Nargund, Oncology, p. 559, Oct. 2012.*
Jelmyto, LG-UTUC p. 1, Apr. 2020.*
Shanna , UROToday, Non-Muscle Invasive Bladder Cancer, p. 1-5, Sep. 2012.*
Chong, Urology Journal, cold-cup biopsy, p. 46 Feb. 2018.*
Porta UGN-101, Opinion On Pharmaco. p. 2199, Sep. 2020.*
Chevli, LG IR NMIBC, J. Urology, p. 61, Jan. 2022.*
Porten, Chemo. NMIBC, Indian J. Uro., p. 297, Oct. 2015.*
UroGen, Rep, UGN-101 and UGN-102, p. 1 Sep. 2019.*
H.T. Ta, et al., "Injectable chitosan hydrogels for localised cancer therapy", Journal of Controlled Release, vol. 126, pp. 205-216 (2008).
C.P. Calderon, et al., "Deep Convolutional Neural Network Analysis of Flow Imaging Microscopy Data to Classify Subvisible Particles in Protein Formulations", Journal of Pharmaceutical Sciences, vol. 107, pp. 999-1008 (2018).

(Continued)

*Primary Examiner* — David J Blanchard
*Assistant Examiner* — Thurman Wheeler
(74) *Attorney, Agent, or Firm* — VENABLE LLP

(57) ABSTRACT

A method of reducing risk of bladder tumor recurrence, progression or death, or a method of increasing probability of disease-free survival at 15 months post-treatment, or a method of increasing probability of maintaining an achieved complete response for at least 15 months post-treatment comprises administering to a patient in need thereof a thermally gelling pharmaceutical composition once weekly for six weeks, the patient having low-grade intermediate-risk non-muscle invasive bladder cancer, and the thermally gelling pharmaceutical composition comprising a reverse thermal gelation agent, a polymer, and mitomycin. The risk is reduced or the probability is increased in comparison to the risk or probability expected if the patient were instead to receive TURBT monotherapy as treatment.

4 Claims, 11 Drawing Sheets

(56) References Cited

OTHER PUBLICATIONS

Y. You, et al., "Intraoperative Mitomycin C in Dacryocystorhinostomy", Opthalmic Plastic and Reconstructive Surgery, vol. 17, No. 2, pp. 115-119 (2001).

H. Wang, U.S. Pharmacopeia, http://www.pharmacopeia.cn/v29240/usp29nf24s0_m66210.html, vol. 29, No. 6, p. 2020 (2007), retrieved from the internet on Feb. 21, 2024.

X. Gao, et al., "Bladder Tissue Uptake of Mitomycin C during Intravesical Therapy Is Linear with Drug Concentration in Urine", Clinical Cancer Research, vol. 3, pp. 139-143 (1998).

T.D. Schmittgen, et al., "Pharmacodynamics of Mitomycin C in Cultured Human Bladder Tumors", Cancer Research, vol. 51, pp. 3849-3856 (1991).

Technical Bulletin, Pluronic Block Copolymer NF Grades (Poloxamer NF Grades), BASF The Chemical Company, 2 pages (2002).

S. Miyazaki, et al., "Antitumor Effect of Pluronic F-127 Gel Containing Mitomycin C on Sarcoma-180 Ascites Tumor in Mice", Chem. Pharm. Bull. 40(8) 2224-2226 (1992).

E. Bilensoy, et al., "Mucoadhesive, Thermosensitive, Prolonged-Release Vaginal Gel for Clotrimazole: beta-Cyclodextrin Complex", AAPS PharmSciTech 2006; 7(2) Article 38 (http://www.aapspharmscitech.org).

JELMYTO (mitomycin) [package insert]. Princeton, NJ: UroGen Pharma, Inc; Apr. 2020.

International Search Report dated Jan. 18, 2012, in corresponding PCT/IL2011/000069 (7 pages).

Written Opinion dated Jan. 18, 2012, in corresponding PCT/IL2011/000069 (12 pages).

A. Rey-Rico, et al., "PEO-PPO-PEO Tri-Block Copolymers for Gene Delivery Applications in Human Regenerative Medicine—An Overview", Int. J. Mol. Sci. 2018, 19, 775.

K.K. Chevli, et al., "Primary Chemoablation of Low-Grade Intermediate-Risk Nonmuscle-Invasive Bladder Cancer Using UGN-102, a Mitomycin-Containing Reverse Thermal Gel (Optima II): A Phase 2b, Open-Label, Single-Arm Trial", J. Urol., vol. 207, pp. 61-69 (2022).

A.M. Stover, et al., "Minimal Patient-Reported Side Effects for a Chemoablative Gel (UGN-102) Used as Frontline Treatment in Adults with Nonmuscle-Invasive Bladder Cancer", J. Urol., vol. 208, pp. 580-588 (2022).

R.S. Matulewicz, et al., "The effect of surgical duration of transurethral resecton of bladder tumors on postoperative complications: An analysis of ACS NSQIP data", Urologic Oncology: Seminars and Original Investigations 33 (2015) 338.e19-338.e24.

J.F. Pereira, et al., "The Perioperative Morbidity of Transurethral Resection of Bladder Tumor: Implications for Quality Improvement", Urology 125: 131-137, 2019.

M.S. Erikson, et al., "Do repeated transurethral procedures under general anesthesia influence mortality in patients with non-invasive urothelial bladder cancer? A Danish national cohort study", Scandinavian Journal of Urology, 2020, vol. 54, No. 4, 281-289.

Holzbeierlein J, Bixler BR, Buckley DI, et al. Treatment of non-metastatic muscle-invasive bladder cancer: AUA/ASCO/SUO guideline (2017; amended 2020, 2024). J Urol. Published online Apr. 25, 2024.

M.S. Lindgren, et al., "DaBlaCa-13 Study: Oncological Outcome of Short-Term, Intensive Chemoresection with Mitomycin in Nonmuscle Invasive Bladder Cancer: Primary Outcome of a Randomized Controlled Trial", Journal of Clinical Oncology, vol. 41, Issue 2, p. 206-211, PY 2022.

A. Sankin, et al., "Low-grade Urothelial Carcinoma Recurs at a Tempo that Naturally Accelerates Over Time", Urology, 2024 193:166-172.

S. Vacas, et al., "Cognitive Decline Associated with Anesthesia and Surgery in Older Patients", JAMA 326(9): 863-864 (2021).

UroGen Pharma," Zusduri Median Duration of Response Still Not Reached with 64.5% 36-month Duration of Response in the Pivotal ENVISION Trial", May 2026, 3 pages.

* cited by examiner

Fig. 4

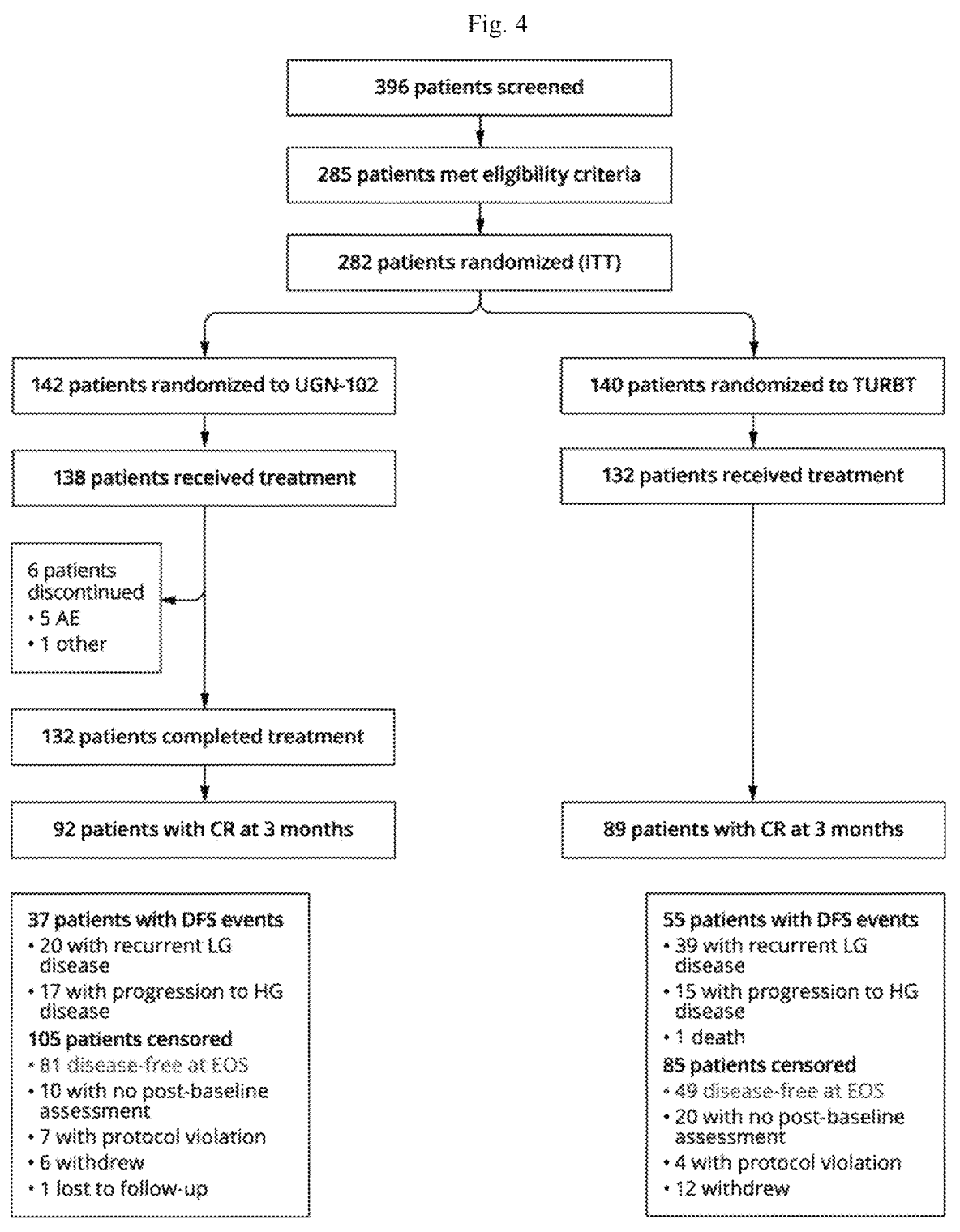

396 patients screened 285 patients met eligibility criteria 282 patients randomized (ITT)

142 patients randomized to UGN-102

138 patients received treatment 6 patients discontinued
- 5 AE
- 1 other 132 patients completed treatment 92 patients with CR at 3 months 37 patients with DFS events
- 20 with recurrent LG disease
- 17 with progression to HG disease 105 patients censored
- 81 disease-free at EOS
- 10 with no post-baseline assessment
- 7 with protocol violation
- 6 withdrew
- 1 lost to follow-up 140 patients randomized to TURBT 132 patients received treatment 89 patients with CR at 3 months 55 patients with DFS events
- 39 with recurrent LG disease
- 15 with progression to HG disease
- 1 death 85 patients censored
- 49 disease-free at EOS
- 20 with no post-baseline assessment
- 4 with protocol violation
- 12 withdrew

TREATMENT OF LOW-GRADE INTERMEDIATE-RISK NON-MUSCLE-INVASIVE BLADDER CANCER WITH A THERMALLY GELLING PHARMACEUTICAL COMPOSITION CONTAINING MITOMYCIN

This application claims the benefit of U.S. Provisional Application Nos. 63/515,352, filed Jul. 25, 2023, and 63/640,252, filed Apr. 30, 2024, the entire contents of each of which is incorporated by reference herein.

FIELD OF THE INVENTION

The disclosure relates to the treatment of low-grade intermediate-risk non-muscle invasive bladder cancer (LG IR NMIBC) by administration to the bladder of a patient in need thereof of a thermally gelling pharmaceutical composition comprising mitomycin.

BACKGROUND OF THE INVENTION

Bladder cancer is the second most common urologic cancer in men, with about 730,000 people in the U.S. living with bladder cancer. Cancer Stat Facts: Bladder Cancer. National Cancer Institute: Surveillance, Epidemiology, and End Results Program. Accessed Jun. 5, 2024 (data as of 2021). https://seer.cancer.gov/statfacts/html/urinb.html. Between 2019 and the third quarter of 2020, about 93,000 TURBT (transurethral resection of bladder tumor) procedures were performed in outpatient settings in the U.S. TURBT is a surgical procedure used in both the diagnosis and treatment of bladder cancer. This procedure allows a surgeon to biopsy a patient's tumor, or remove an entire small tumor from the inside of the patient's bladder, while leaving the bladder intact. This procedure is essential to obtain a biopsy to confirm the cancer diagnosis and determine the stage and grade of a patient's cancer. At the start of the procedure, a patient is given an anesthetic (numbing drug) either as general anesthesia, where the patient is unconscious for the entire procedure, or local anesthesia, where the patient remains awake, but a local anesthetic drug is administered through a needle in their back to numb the lower half of their body. The surgeon then inserts a tool (a resectoscope) through the urethra to reach the inside of the patient's bladder. A surgical loop on the tool is used to resect, or cut off, a sample of tumor tissue to be analyzed by a pathologist, or to resect the entire tumor from a patient's bladder if the tumor is small enough. TURBT is used as a treatment for patients with early-stage bladder cancer and can be followed by intravesical therapy, which is a procedure in which physicians place liquid anti-cancer medication directly into the patient's bladder. The current treatment paradigm for bladder cancer, one of the most recurrent of all cancers, is lacking.

There are several distinct types of bladder cancer including non-muscle-invasive bladder cancer (NMIBC) and muscle-invasive bladder cancer (MIBC). NMIBC consists of three groups: (Tis), (Ta) and (T1). Tis is a flat, non-invasive carcinoma and is also known as flat carcinoma in situ (CIS). The cancer is growing in the inner lining layer of the bladder only. It has not grown inward toward the hollow part of the bladder, nor has it invaded the connective tissue or muscle of the bladder wall. Ta is a non-invasive papillary carcinoma which has grown toward the hollow center of the bladder but has not grown into the connective tissue or muscle of the bladder wall. It has not spread to nearby lymph nodes (NO) or distant sites (MO). T1 is a bladder cancer that is still localized or contained within the urothelium layer lining the wall of the bladder. Cancer cells have not invaded the deeper layers of bladder wall tissue. T1 means the tumor has grown from the layer of cells lining the bladder into the connective tissue below. It has not grown into the muscle layer of the bladder. MIBC consists of three groups: (T2), (T3) and (T4). A T2 bladder cancer has invaded the muscle layer of the bladder but not deeper. Stage T3 cancer has grown through the bladder muscle into the fat layer surrounding the bladder, while stage T4 cancer has grown directly into nearby organs.

Each of the types of bladder cancer has different risks associated with it. Below is a depiction of the American Urological Association (AUA) Risk Stratification for Non-muscle Invasive Bladder Cancer.

| Low Risk | Intermediate Risk | High Risk |
|---|---|---|
| LG[a] solitary Ta ≤3 cm<br>PUNLMP[b] | Recurrence within 1 year, LG Ta<br>Solitary LG Ta >3 cm<br>LG Ta, multifocal<br>HG[c] Ta, ≤3 cm<br>LG T1 | HG T1<br>Any recurrent, HG Ta<br>HG Ta, >3 cm (or multifocal)<br>Any CIS[d]<br>Any BCG failure in HG patient<br>Any variant histology<br>Any LVI[e]<br>Any HG prostatic urethral involvement |

[a]LG = low grade;
[b]PUNLMP = papillary urothelial neoplasm of low malignant potential;
[c]HG = high grade;
[d]CIS = carcinoma in situ;
[e]LVI = lymphovascular invasion Low-grade intermediate-risk non-muscle-invasive bladder cancer (LG IR NMIBC) is one such category of bladder cancer. In 2023, LG NMIBC will account for approximately 50% of the aggregate bladder cancer disease burden in the United States. Siegel, et al., CA Cancer J Clin. 2023; 73(1):17-48. Management of LG NMIBC is performed primarily by TURBT under anesthesia. Chang, et al., J Urol. 2016; 196(4):1021-1029. Recurrence of disease following TURBT is common, particularly for patients with intermediate risk (TR) cancer. This is due to multiple factors, including the biology of urothelial cancers with asynchronous malignant transformation of normal appearing urothelium and incomplete surgical removal of visible tumor. Lotan, et al., Nat Rev Urol. 2019; 16(6):377-386; Strandgaard, et al., bioRxiv. 2023:2023.2002.2020.528920; and Tan, et al., Eur Urol Oncol. 2022; 5(5):505-516. Both the AUA and National Comprehensive Cancer Network recommend adjuvant immunotherapy or chemotherapy following TURBT for IR NMIBC patients, but real-world evidence suggests that compliance with this recommendation is modest in the U.S. Lewicki, et al., JAMA Netw Open. 2022; 5(3):e220602; Mori, et al., Urol Oncol. 2020; 38(10):774-782; and Tobert, et al., Urology. 2019; 132:150-155. Treating LG IR NMIBC also poses a number of challenges due to the heterogeneous nature of the population, uncertainty when categorizing patients, and the lack of independent studies comparing therapies.

Since the risk of disease progression is low, but risk of recurrence is high, in LG NMIBC, improved methods aimed at optimizing disease clearance and forestalling recurrence to avoid risks of repetitive surgery and anesthesia are needed. Tan, et al.; Erikson, et al., Scand J Urol. 2020; 54(4):281-289; and Lenis, et al., JAMA. 2020; 324(19): 1980-1991. In fact, NMIBC patients can find themselves in a frustrating cycle of treatments, with about 68% of recurrent patients having 2 or more recurrences and about 23% of recurrent patients having 5 or more recurrences. Having repeat surgery results in risks to patients with this condition. About 33% of patients will experience an adverse event within 90 days of undergoing a TURBT. Sharma, et al., J Urol. 2021:206. Patients with LG IR NMIBC who have multiple recurrences carry a 10-20% risk of progression. Sharma, et al., Urology. 2023; 173:134-141. LG IR NMIBC patients who had 2-4 procedures had a 14% greater risk of death than patients who only had one procedure. Erikson, et al., Scand J Urol. 2020; 54(4):281-289.

As noted above, most patients experience recurrence after endoscopic surgical treatment, and repeat TURBT is the current standard of care for patients who experience non-invasive intravesical relapse. TURBT is associated with well-known risks that include failure to cure, bleeding requiring unplanned hospital admission and bladder perforation. Pereira, et al., Urology 2019; 125: 131-137; DeNunzio, et al., Eur J Surg Oncol 2014; 40: 90; Ghali, et al., Scand J Urol 2016; 50: 370; Matulewicz, et al., Urol Oncol 2015; 33: 338; Patel, et al., Urology 2015; 85: 552; and Rambachan, et al., J Urol 2014; 192: 183. In addition, recently published evidence suggests that repetitive TURBT is independently associated with an increased mortality risk. Erickson, et al. Repetitive surgical procedures under anesthesia carry additional risk, particularly for those of advanced age, for whom the repeated use of general anesthesia may predispose to cognitive decline. Strandgaard, et al.; Evered, et al., J Alzheimers Dis. 2018; 66(1): 1-10; Greaves, et al., Int J Cardiol 2019; 289: 43; and Krause, et al., BMJ 2019; 366:14466.

The search for alternatives to TURBT has evolved over the past several decades. Electromotive drug administration and chemothermotherapy have been explored with early success in the treatment of refractory HG NMIBC but have not been successfully applied to IR papillary disease. Melgarejo-Segura, et al., Urol Oncol. 2023; 41(4):166-176; and Zhao, et al., Front Surg. 2021; 8:775527. Others have shown that the efficacy of intravesical drug treatment of urothelial cancer is directly related to increasing drug concentration and dwell time. Au, et al., J Natl Cancer Inst. 2001; 93(8):597-604; Dalton, et al., Cancer Res. 1991; 51(19): 5144-5152; Wientjes, et al., Cancer Res. 1993; 53(14):3314-3320; Angulo, et al., Eur Urol Oncol. 2023; 6(1):58-66; and Tan, et al., Eur Urol. 2023; 83(6):497-504. Recent studies employing dose-intensive administration of aqueous mitomycin as primary therapy for LG NMIBC demonstrate the validity of this observation, achieving CR rates ranging from 50-60%, but required frequent drug administration at short intervals that is cumbersome and impractical for routine patient care. Colombo, et al., Eur Urol. 2012; 62(5):797-802; Lindgren, et al., J Clin Oncol. 2023; 41(2):206-211; and Yanagisawa, et al., Eur Urol Focus. 2023; 9(3):463-479.

Reverse thermal gels are useful for drug delivery and are particularly well-suited for use in the urinary tract where dilution by continuous urine production and excretion by bladder contraction limit the therapeutic effect of aqueous medications.

UGN-101 (UroGen Pharma), a reverse thermal gel containing mitomycin (4 mg/ml) is approved by the U.S. Food and Drug Administration for the treatment of low grade upper tract urothelial carcinoma (LG UTUC) and has recently been incorporated into AUA UTUC guidelines to promote renal preservation. Mitomycin C (also referred to as MMC or MUTAMYCIN®) is a methylazirinopyrroloindoledione antineoplastic antibiotic isolated from the bacterium *Streptomyces caespitosus* and other *Streptomyces* bacterial species. The extended dwell time for mitomycin of 4-6 hours facilitates primary chemoablation with initial complete response (CR) rates ranging from 57% to 70%, good duration of response (DOR), and an acceptable safety profile. UGN-101 is administered into the upper tract either retrograde under fluoroscopic guidance or antegrade via a nephrostomy tube.

UGN-102 (UroGen Pharma) is also a reverse thermal gel comprising mitomycin at a lower concentration (1.33 mg/ml). Its administration is different than UGN-101 since it can be delivered via urethral catheter in an ambulatory setting. The instilled volume of approximately 60 ml delivers twice the dose of mitomycin that is administered in aqueous solution for adjuvant therapy and disintegrates over a period of up to 6 hours with gel fragments excreted during normal voiding.

SUMMARY OF THE DISCLOSURE

The present disclosure provides a method of reducing risk of bladder tumor recurrence, progression or death comprising the step of administering to a patient in need thereof a thermally gelling pharmaceutical composition once weekly for six weeks, wherein the patient has low-grade intermediate-risk non-muscle invasive bladder cancer, wherein the thermally gelling pharmaceutical composition comprises a reverse thermal gelation agent, a polymer selected from the group consisting of cellulose, microcrystalline cellulose, cellulose derivatives, and combinations thereof, and mitomycin, and wherein the risk is reduced in comparison to a risk expected if the patient were instead to receive TURBT monotherapy as treatment. In some embodiments, the thermally gelling pharmaceutical composition comprises Poloxamer 407, hydroxypropylmethylcellulose, and mitomycin.

The present disclosure also provides a method of increasing probability of disease-free survival at 15 months post-treatment comprising the step of: administering to a patient in need thereof a thermally gelling pharmaceutical composition once weekly for six weeks, wherein the patient has low-grade intermediate-risk non-muscle invasive bladder cancer, wherein the thermally gelling pharmaceutical composition comprises a reverse thermal gelation agent, a polymer selected from the group consisting of cellulose, microcrystalline cellulose, cellulose derivatives, and combinations thereof, and mitomycin, and wherein the probability is increased in comparison to a probability expected if the patient were instead to receive TURBT monotherapy as treatment. In some embodiments, the thermally gelling pharmaceutical composition comprises Poloxamer 407, hydroxypropylmethylcellulose, and mitomycin.

The present disclosure also provides a method of increasing probability of maintaining an achieved complete response for at least 15 months post-treatment comprising the step of: administering to a patient in need thereof a thermally gelling pharmaceutical composition once weekly for six weeks, wherein the patient has low-grade intermediate-risk non-muscle invasive bladder cancer, wherein the thermally gelling pharmaceutical composition comprises a reverse thermal gelation agent, a polymer selected from the group consisting of cellulose, microcrystalline cellulose, cellulose derivatives, and combinations thereof, and mitomycin, and wherein the probability is increased in comparison to a probability expected if the patient were instead to receive TURBT monotherapy as treatment. In some embodiments, the thermally gelling pharmaceutical composition comprises Poloxamer 407, hydroxypropylmethylcellulose, and mitomycin.

In some embodiments of these methods, the patient has had TURBT for treatment of non-muscle invasive bladder cancer at any time prior to the administration of the gel comprising mitomycin. In some embodiments of these methods, the patient has not had TURBT for treatment of non-muscle invasive bladder cancer at any time prior to the administration of the gel comprising mitomycin.

In some embodiments of these methods, the thermally gelling pharmaceutical composition comprises 75 mg of mitomycin.

BRIEF DESCRIPTION OF THE FIGURES

FIG. 4 is a flow diagram for patient enrollment in the ATLAS study.

DETAILED DESCRIPTION OF THE INVENTION

Figure 1:
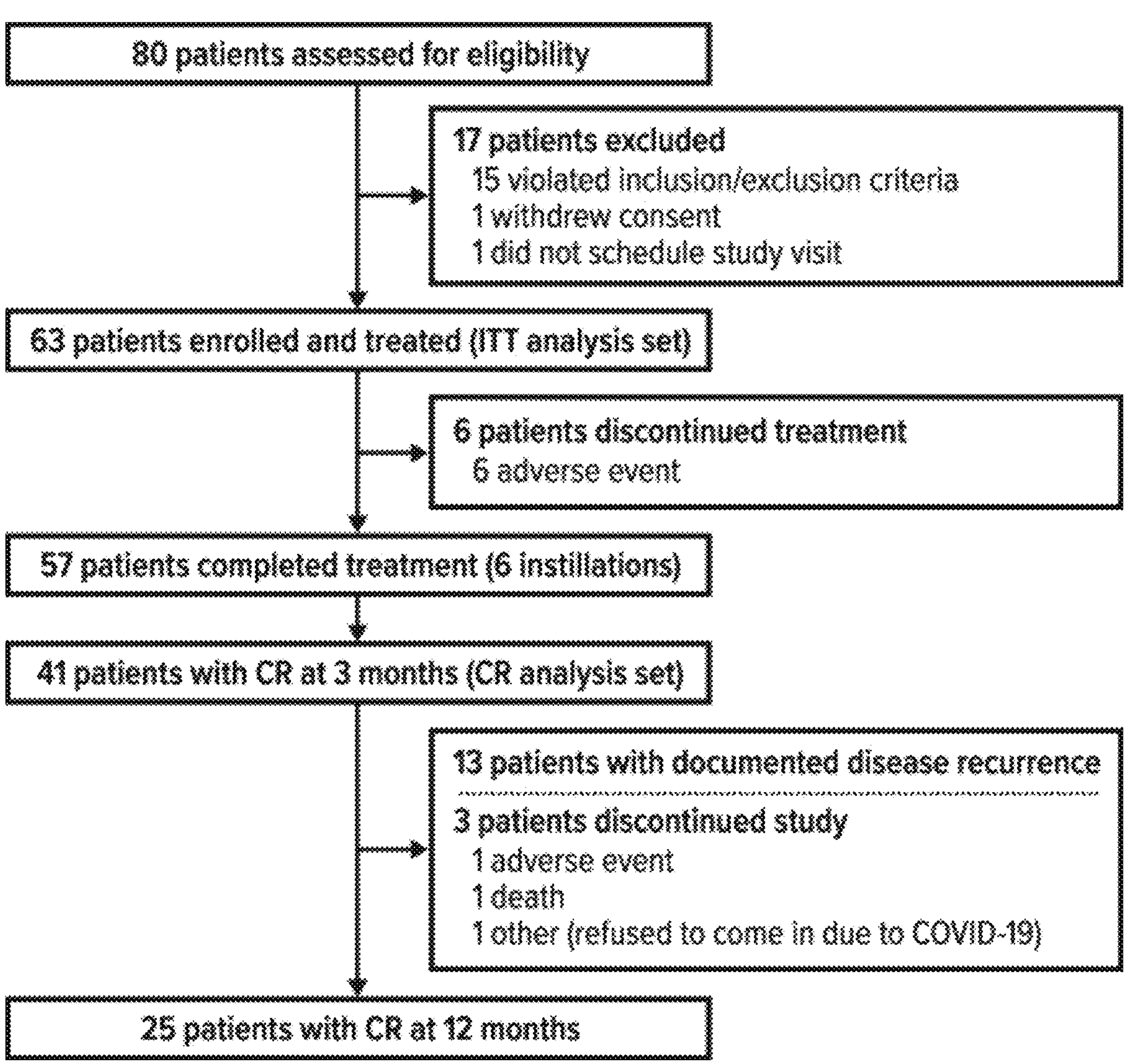
FIG. 1 is a flow diagram for patient enrollment in the OPTIMA II study.

This disclosure relates to the treatment of low-grade intermediate-risk non-muscle invasive bladder cancer (LG IR NMIBC) by administration to the bladder of a patient in need thereof of a thermally gelling pharmaceutical composition comprising mitomycin.

One embodiment of the disclosure is directed to a method of reducing risk of bladder tumor recurrence, progression or death comprising the step of: administering to a patient in need thereof a thermally gelling pharmaceutical composition once weekly for six weeks, wherein the patient has low-grade intermediate-risk non-muscle invasive bladder cancer, wherein the thermally gelling pharmaceutical composition comprises a reverse thermal gelation agent, a polymer selected from the group consisting of cellulose, microcrystalline cellulose, cellulose derivatives, and combinations thereof, and mitomycin, and wherein the risk is reduced in comparison to a risk expected if the patient were instead to receive TURBT monotherapy as treatment. In some embodiments, the thermally gelling pharmaceutical composition comprises Poloxamer 407, hydroxypropylmethylcellulose, and mitomycin.

"Reducing risk of bladder tumor recurrence, progression or death" refers to lowering the chance that any of bladder tumor recurrence, progression of disease, i.e., LG IR NMIBC, or death occurs. "Reducing" simply refers to a lessening of risk by any degree.

"Bladder tumor recurrence" refers to a tumor in the bladder that returns after it has been treated or after it has disappeared as a result of treatment.

"Progression" refers to progression of disease, in this case LG IR NMIBC, i.e., worsening in grade or stage of disease or spread of disease in the body.

"Administering" or "administration" refers the act of providing or the provision of the thermally gelling pharmaceutical composition to the patient in need thereof. According to this disclosure, the thermally gelling pharmaceutical composition is administered by intravesical instillation to the bladder of the patient. In some embodiments, the thermally gelling pharmaceutical composition is administered via a catheter or any other means effective. According to this disclosure, the thermally gelling pharmaceutical composition is administered once weekly for six weeks. In some embodiments, from 25 mL to 100 mL, or 45 mL to 85 mL, or 55 mL to 65 mL, or about 56 mL, or about 60 mL, of the thermally gelling pharmaceutical composition is administered. In some embodiments, six once-weekly intravesical instillations of UGN-102 (75 mg mitomycin in 56 ml admixture with a reverse thermal hydrogel to equal 1.33 mg/ml) are administered to a patient in need thereof.

A "patient in need thereof" refers to a person in need of, or desirous of, treatment for disease, in this case LG IR NMIBC. As used herein, a "patient in need thereof" encompasses both a determination of need for treatment by a medical professional as well as a desire of a patient for such treatment. In some embodiments, the patient may have had TURBT for treatment of NMIBC at any time prior to the administration of the thermally gelling pharmaceutical composition. In some embodiments, the patient may not have had TURBT for treatment of NMIBC at any time prior to the administration of the thermally gelling pharmaceutical composition. In some embodiments, the patient may have had a previous diagnosis of NMIBC and have been treated for NMIBC. In some embodiments, the patient may presently have a first diagnosis of NMIBC.

As used in this embodiment, a "patient in need thereof" refers to being in need of the stated objective or intentional purpose expressed, i.e., being in need of reducing risk of bladder tumor recurrence, progression or death; "administering to a patient in need thereof" requires administering the thermally gelling pharmaceutical composition with the intent to achieve the stated objective or intentional purpose expressed, i.e., being in need of reducing risk of bladder tumor recurrence, progression or death.

Low-grade intermediate-risk non-muscle invasive bladder cancer (LG IR NMIBC) refers to NMIBC classified as low-grade and intermediate-risk when classified by a classification system such as the above-described American Urological Association (AUA) Risk Stratification for Non-muscle Invasive Bladder Cancer.

The thermally gelling pharmaceutical composition is a combination of mitomycin and a thermoreversible hydrogel comprising a reverse thermal gelation agent and a polymer selected from the group consisting of cellulose, microcrystalline cellulose, cellulose derivatives, and combinations thereof. A thermoreversible hydrogel (and thus the thermally gelling pharmaceutical composition) is liquid at low temperatures (e.g., at about 5° C.) and solidifies at higher temperatures (e.g., above about 14° C.); in some embodiments, the thermoreversible hydrogel (and thus the thermally gelling pharmaceutical composition) is solid in vivo.

As used herein, "thermally gelling pharmaceutical composition", "thermally gelling mitomycin C composition", and "thermally gelling composition" are used interchangeably. As used herein, "thermoreversible hydrogel" and "thermally gelling hydrogel" are used interchangeably.

The thermally gelling pharmaceutical composition of the present disclosure comprises at least one reverse thermal gelation agent. In some embodiments, the reverse thermal gelation agent is an ethylene oxide/propylene oxide block copolymer such as a Poloxamer. In some embodiments of the disclosure, the reverse thermal gelation agent is Poloxamer 407. In some embodiments, the reverse thermal gelation agent is present in the thermally gelling pharmaceutical composition in an amount of from about 15% to about 35%, or from about 20% to about 30%, or from about 23% to about 27%, or from about 24% to about 25%, or about 24% (w/w) based on a total weight of the thermally gelling pharmaceutical composition.

The thermally gelling pharmaceutical composition of the present disclosure comprises at least one polymer selected from the group consisting of cellulose, microcrystalline cellulose, cellulose derivatives, and combinations thereof. In some embodiments, the polymer is hydroxypropylmethylcellulose. In some embodiments, the polymer is present in the thermally gelling pharmaceutical composition in an amount of from about 0.01% to about 5%, or from about 0.015% to about 0.2%, or from about 0.15% to about 0.18%, (w/w), or from about 0.15% to about 0.16% (w/w) based on a total weight of the thermally gelling pharmaceutical composition.

In some embodiments, the thermally gelling pharmaceutical composition comprises additional components such as polyethylene glycol, e.g., PEG-400, water, and mitomycin bulking agents, e.g., mannitol or urea. PEG-400 is present in the thermally gelling pharmaceutical composition in an amount of from about 0% to about 2.5%, or from about 0.1% to about 1.8%, (w/w) based on a total weight of the thermally gelling pharmaceutical composition.

Mitomycin (also referred to as mitomycin C, MMC or MUTAMYCIN®) is a methylazirinopyrroloindoledione antineoplastic antibiotic isolated from the bacterium *Streptomyces caespitosus* and other *Streptomyces* bacterial species. In some embodiments, an amount of mitomycin in the thermally gelling pharmaceutical composition ranges from greater than 37.5 mg to less than 120 mg, or from 50 mg to 100 mg, or from 60 mg to 90 mg, or from 65 mg to 85 mg. In some embodiments, the thermally gelling pharmaceutical composition comprises 75 mg of mitomycin. In some embodiments of the disclosure, mitomycin is present in an amount of from about 0.1 mg/ml to about 4 mg/ml, or from about 0.5 mg/ml to about 2 mg/ml, or from about 1 mg/ml to about 1.5 mg/ml, or of about 1.33 mg/ml of the thermally gelling pharmaceutical composition.

In some embodiments of the disclosure, the thermally gelling pharmaceutical composition comprises Poloxamer 407, hydroxypropylmethylcellulose, mitomycin, PEG-400, and water. In some embodiments of the disclosure, the thermally gelling pharmaceutical composition comprises Poloxamer 407, hydroxypropylmethylcellulose, mitomycin, PEG-400, water, and mannitol. In some embodiments of the disclosure, the thermally gelling pharmaceutical composition comprises Poloxamer 407, hydroxypropylmethylcellulose, mitomycin, PEG-400, water, and urea. In some embodiments, the thermally gelling pharmaceutical composition is a gel as set forth in any of U.S. Pat. Nos. 9,040,074, 9,950,069, and U.S. Patent Application Publication No. 2022/0202773, the disclosure of each of which is incorporated by reference herein. In some embodiments, the thermally gelling pharmaceutical composition is UGN-102.

"TURBT monotherapy" refers to the use of TURBT as the only therapy for the treatment of disease, in this case LG IR NMIBC.

Another embodiment of the disclosure is directed to a method of increasing probability of disease-free survival at 15 months post-treatment comprising the step of: administering to a patient in need thereof a thermally gelling pharmaceutical composition once weekly for six weeks, wherein the patient has low-grade intermediate-risk non-muscle invasive bladder cancer, wherein the thermally gelling pharmaceutical composition comprises a reverse thermal gelation agent, a polymer selected from the group consisting of cellulose, microcrystalline cellulose, cellulose derivatives, and combinations thereof, and mitomycin, and wherein the probability is increased in comparison to a probability expected if the patient were instead to receive TURBT monotherapy as treatment. In some embodiments, the thermally gelling pharmaceutical composition comprises Poloxamer 407, hydroxypropylmethylcellulose, and mitomycin.

"Increasing probability of disease-free survival" refers to increasing the chance that a patient survives without any signs or symptoms of disease. "Disease-free survival" is defined as the time from first dose, in this case, the first of six weekly administrations, to the earliest date of recurrence or progression or death due to any cause, whichever occurred first. Alternatively "disease-free survival" is defined as the time from randomization in a clinical trial to the earliest date of recurrence or progression or death due to any cause, whichever occurred first. "Increasing" simply refers to growing or making greater by any degree.

"Post-treatment" refers to the period of time after the first dose, in this case, the first of six weekly administrations, or after TURBT.

All details above, e.g., regarding the administration step, the thermally gelling pharmaceutical composition, the LG IR NMIBC, mitomycin, and TURBT monotherapy, are the same for this embodiment.

As used in this embodiment, a "patient in need thereof" refers to being in need of the stated objective or intentional purpose expressed, i.e., being in need of increasing probability of disease-free survival at 15 months post-treatment; "administering to a patient in need thereof" requires administering the thermally gelling pharmaceutical composition with the intent to achieve the stated objective or intentional purpose expressed, i.e., being in need of increasing probability of disease-free survival at 15 months post-treatment.

Another embodiment of the disclosure is directed to a method of increasing probability of maintaining an achieved complete response for at least 15 months post-treatment comprising the step of: administering to a patient in need thereof a thermally gelling pharmaceutical composition once weekly for six weeks, wherein the patient has low-grade intermediate-risk non-muscle invasive bladder cancer, wherein the thermally gelling pharmaceutical composition comprises a reverse thermal gelation agent, a polymer selected from the group consisting of cellulose, microcrystalline cellulose, cellulose derivatives, and combinations thereof, and mitomycin, and wherein the probability is increased in comparison to a probability expected if the patient were instead to receive TURBT monotherapy as treatment. In some embodiments, the thermally gelling pharmaceutical composition comprises Poloxamer 407, hydroxypropylmethylcellulose, and mitomycin.

"Increasing probability of maintaining an achieved complete response" refers to increasing the chance that a patient exhibits no signs or symptoms of disease, in this case LG IR NMIBC. "Complete response" or CR is defined as having no detectable disease, in this case LG IR NMIBC, in the bladder. "Increasing" simply refers to growing or making greater by any degree.

All details above, e.g., regarding the administration step, the thermally gelling pharmaceutical composition, the LG IR NMIBC, mitomycin, TURBT monotherapy, and post-treatment, are the same for this embodiment.

As used in this embodiment, a "patient in need thereof" refers to being in need of the stated objective or intentional purpose expressed, i.e., being in need of increasing probability of maintaining an achieved complete response for at least 15 months post-treatment; "administering to a patient in need thereof" requires administering the thermally gelling pharmaceutical composition with the intent to achieve the stated objective or intentional purpose expressed, i.e., being in need of increasing probability of maintaining an achieved complete response for at least 15 months post-treatment.

Other embodiments of the disclosure are as set forth below. In certain embodiments, the thermally gelling pharmaceutical composition of the embodiments above may take the form of any of the mitomycin C compositions, i.e., any of the below compositions which include mitomycin C, of the embodiments below.

Embodiment 1. A method of treating recurrent low grade intermediate risk non-muscle-invasive bladder cancer in a patient comprising administering into the bladder of the patient 45-85 mL of a thermally gelling mitomycin C composition comprising about 75 mg of mitomycin C.

Embodiment 2. The method of Embodiment 1, wherein said administering is carried out once weekly for six weeks.

Embodiment 3. The method of any of Embodiments 1 or 2, wherein the thermally gelling mitomycin C composition is prepared within 14 days of said administering by mixing mitomycin C together with a thermally gelling hydrogel, and wherein said thermally gelling hydrogel comprises:

27% Poloxamer 407, 0.18% HPMC,

1% PEG-400, and water.

Embodiment 4. The method of Embodiment 3, wherein the mitomycin C is wetted with the thermally gelling hydrogel prior to said mixing.

Embodiment 5. The method of Embodiment 4, wherein the thermally gelling hydrogel is diluted with water prior to said mixing.

Embodiment 6. The method of any of Embodiments 3-5, wherein the thermally gelling mitomycin C composition is prepared within 48 hours of said administering.

Embodiment 7. The method of any of Embodiments 1-6, wherein the thermally gelling mitomycin C composition is stored at a temperature below about 8° C. prior to said administering.

Embodiment 8. The method of any of Embodiments 1-7, wherein the thermally gelling mitomycin C composition is stored at a temperature ranging from about 2-8° C. prior to said administering.

Embodiment 9. The method of any of Embodiments 3-8, wherein 80 mg of mitomycin C is mixed with 60 mL of the thermally gelling hydrogel.

Embodiment 10. The method of any of Embodiments 1-9 wherein the volume of thermally gelling mitomycin C composition administered is about 56 mL.

Embodiment 11. The method of any of Embodiments 1-10, wherein said administering is to a patient following TURBT surgery.

Embodiment 12. The method of any of Embodiments 1-11, wherein the patient has a single tumor or multifocal tumors.

Embodiment 13. A method of reducing bladder tumor recurrence, progression, or death in a population of patients suffering from recurrent low grade intermediate risk non-muscle-invasive bladder cancer, comprising administering into the bladder of each of the patients in the population 45-85 mL of a thermally gelling composition comprising 60 mg to 120 mg, or 75 mg, of mitomycin C, wherein 6-18 months after said administering, the population of patients has about a 70% reduced risk of bladder tumor recurrence, progression, or death compared to an otherwise equivalent population of patients suffering from recurrent low grade intermediate risk non-muscle-invasive bladder cancer who have received only TURBT therapy.

Embodiment 14. The method of Embodiment 13, wherein said administering is carried out once weekly for six weeks.

Embodiment 15. The method of any of Embodiments 13 or 14, wherein the thermally gelling composition is prepared within 14 days of said administering by mixing mitomycin C together with a thermally gelling hydrogel, wherein said thermally gelling hydrogel comprises:

27% Poloxamer 407, 0.18% HPMC,

1% PEG-400, and water.

Embodiment 16. The method of Embodiment 15, wherein the mitomycin C is wetted with the thermally gelling hydrogel prior to said mixing.

Embodiment 17. The method of Embodiment 16, wherein the thermally gelling hydrogel is diluted with water prior to said mixing.

Embodiment 18. The method of any of Embodiments 15-17, wherein the thermally gelling composition is prepared within 48 hours of said administering.

Embodiment 19. The method of any of Embodiments 13-18, wherein the thermally gelling mitomycin C composition is stored at a temperature below about 8° C. prior to said administering.

Embodiment 20. The method of any of Embodiments 13-19, wherein the thermally gelling mitomycin C composition is stored at a temperature ranging from about 2-8° C. prior to said administering.

Embodiment 21. The method of any of Embodiments 15-20, wherein 80 mg of mitomycin C is mixed with 60 mL of the thermally gelling hydrogel.

Embodiment 22. The method of any of Embodiments 13-21 wherein the volume of thermally gelling composition administered is about 56 mL.

Embodiment 23. The method of any of Embodiments 13-22, wherein said administering is to a patient following TURBT surgery.

Embodiment 24. The method of any of Embodiments 13-23, wherein the patient has a single tumor or multifocal tumors.

Embodiment 25. A pharmaceutically acceptable thermally gelling hydrogel comprising:

27% Poloxamer 407, 0.18% HPMC,

1% PEG-400, and water.

Embodiment 26. A pharmaceutically acceptable thermally gelling hydrogel consisting essentially of:

27% Poloxamer 407,
0.18% HPMC,
1% PEG-400, and
water.

Embodiment 27. The pharmaceutically acceptable thermally gelling hydrogel of Embodiments 25 or 26, wherein no visible precipitation is observed in 70-100 mL of the pharmaceutically acceptable thermally gelling hydrogel after 6 months of storage at 40° C.

Embodiment 28. A thermally gelling pharmaceutical composition comprising:

1.33 mg/mL mitomycin C,
27% Poloxamer 407, or 24.32% Poloxamer 407,
0.18% HPMC, or 0.16% HPMC,
1% PEG-400, or 0.9% PEG-400, and
water.

Embodiment 29. A thermally gelling pharmaceutical composition consisting essentially of:

1.33 mg/mL mitomycin C,
27% Poloxamer 407,
0.18% HPMC,
1% PEG-400, and
water.

Embodiment 30. The thermally gelling pharmaceutical composition of Embodiments 28 or 29, prepared by mixing a sufficient volume of the pharmaceutically acceptable thermally gelling hydrogel of any of Embodiments 25-27 with sufficient mitomycin to provide 45-48 mL of the thermally gelling pharmaceutical composition.

Embodiment 31. The thermally gelling pharmaceutical composition of Embodiment 30, wherein the thermally gelling pharmaceutical composition has a volume of 56 mL and comprises 75 mg mitomycin C.

Embodiment 32. The thermally gelling pharmaceutical composition of any of Embodiments 28-31 for use in treatment of recurrent low grade intermediate risk non-muscle-invasive bladder cancer, wherein after administering 56 mL of the thermally gelling pharmaceutical composition, once weekly for six weeks into the bladders of a population of patients suffering from recurrent low grade intermediate risk non-muscle-invasive bladder cancer, said population of patients exhibits a 70% reduction in risk of recurrence, progression or death from recurrent low grade intermediate risk non-muscle-invasive bladder cancer relative to an otherwise equivalent population of patients suffering from recurrent low grade intermediate risk non-muscle-invasive bladder cancer who have been treated only with TURBT.

Embodiment 33. A method of treating recurrent low grade intermediate risk non-muscle-invasive bladder cancer in a patient, the method comprising administration into the bladder of the patient about 45 to about 85 mL, or about 56 mL, of a thermally gelling mitomycin C composition comprising about 75 mg of mitomycin C.

Embodiment 34. The method of Embodiment 33, wherein said administration is carried out once weekly for six weeks.

Embodiment 35. The method of any of Embodiments 33 or 34, wherein the thermally gelling mitomycin C composition is prepared within 14 days of said administration by mixing mitomycin C together with a thermally gelling hydrogel, and wherein said thermally gelling hydrogel comprises:

about 20% to about 35%, about 25% to about 30%, or about 27% of a poloxamer, preferably the poloxamer is Poloxamer 407, between about 0.15% and 0.20%, preferably between about 0.16% and 0.19%, more preferably between about 0.17% and 0.19%, most preferably about 0.18% HPMC between about 0.5% and 1.5%, between about 0.6% and 1.4%, between about about 0.7% and 1.3%, between about 0.8% and 1.4%, between about 0.9% and 1.1%, or about 1% PEG-400, and water.

Embodiment 36. The method of Embodiment 35, wherein the mitomycin C is wetted with the thermally gelling hydrogel prior to said mixing.

Embodiment 37. The method of Embodiment 36, wherein the thermally gelling hydrogel is diluted with water prior to said mixing.

Embodiment 38. The method of any of Embodiments 35-37, wherein the thermally gelling mitomycin C composition is prepared within about 48 hours of said administration.

Embodiment 39. The method of any of Embodiments 33-38, wherein the thermally gelling mitomycin C composition is stored at a temperature below about 8° C. prior to said administration.

Embodiment 40. The method of any of Embodiments 33-39, wherein the thermally gelling mitomycin C composition is stored at a temperature ranging from about 2° C. to about 8° C. prior to said administration.

Embodiment 41. The method of any of Embodiments 35-40, wherein about 80 mg of mitomycin C is mixed with about 60 mL of the thermally gelling hydrogel.

Embodiment 42. The method of any of Embodiments 33-41 wherein the volume of thermally gelling mitomycin C composition administered is about 56 mL.

Embodiment 43. The method of any of Embodiments 33-42, wherein said administration is to a patient following TURBT surgery.

Embodiment 44. The method of any of Embodiments 33-43, wherein the patient has a single tumor or multifocal tumors.

Embodiment 45. A method of reducing bladder tumor recurrence, progression, or death in a population of patients suffering from recurrent low grade intermediate risk non-muscle-invasive bladder cancer, the method comprising administration into the bladder of each of the patients in the population 45-85 mL of a thermally gelling composition comprising 75 mg of mitomycin C, wherein at least a 50%, a 55%, a 60%, a 65%, a 70% or a 75% reduction in risk of recurrence, progression or death from recurrent low grade intermediate risk non-muscle-invasive bladder cancer at 6 months after treatment, and at least a 25%, a 30%, a 35% or a 40% reduction in risk of recurrence, progression or death from recurrent low grade intermediate risk non-muscle-invasive bladder cancer at one or more of 9, 12, and 15 months after administration of the thermally gelling composition compared to an otherwise equivalent population of patients suffering from recurrent low grade intermediate risk non-muscle-invasive bladder cancer who have received only TURBT therapy.

Embodiment 46. The method of Embodiment 45, wherein said administration is carried out once weekly for six weeks.

Embodiment 47. The method of any of Embodiments 45 or 46, wherein the thermally gelling mitomycin C composition is prepared within about 14 days of said administration by mixing mitomycin C together with a thermally gelling hydrogel, wherein said thermally gelling hydrogel comprises:

about 20% to about 35%, about 25% to about 30%, or about 27% of a poloxamer, preferably the poloxamer is Poloxamer 407, between about 0.15% and about 0.20%, preferably between about 0.16% and about 0.19%, more preferably between about 0.17% and about 0.19%, most preferably about 0.18% HPMC, between about 0.5% and about 1.5%, between about 0.6% and about 1.4%, between about 0.7% and about 1.3%, between about 0.8% and about 1.4%, between about 0.9% and about 1.1%, and about 1% PEG-400, and water.

Embodiment 48. The method of Embodiment 47, wherein the mitomycin C is wetted with the thermally gelling hydrogel prior to said mixing.

Embodiment 49. The method of Embodiment 48, wherein the thermally gelling hydrogel is diluted with water prior to said mixing.

Embodiment 50. The method of any of Embodiments 47-49, wherein the thermally gelling mitomycin C composition is prepared within about 48 hours of said administration.

Embodiment 51. The method of any of Embodiments 45-50, wherein the thermally gelling mitomycin C composition is stored at a temperature below about 8° C. prior to said administration.

Embodiment 52. The method of any of Embodiments 45-51, wherein the thermally gelling mitomycin C composition is stored at a temperature ranging from about 2-8° C. prior to said administration.

Embodiment 53. The method of any of Embodiments 47-52, wherein about 80 mg of mitomycin C is mixed with about 60 mL of the thermally gelling hydrogel.

Embodiment 54. The method of any of Embodiments 35-53 wherein the volume of thermally gelling mitomycin C composition administered is about 56 mL.

Embodiment 55. The method of any of Embodiments 35-54, wherein said administration is to a patient following TURBT surgery.

Embodiment 56. The method of any of Embodiments 35-55, wherein the patient has a single tumor or multifocal tumors.

Embodiment 57. A pharmaceutically acceptable thermally gelling hydrogel comprising:

about 20% to about 35%, about 25% to about 30%, or about 27% of a poloxamer, preferably the poloxamer is Poloxamer 407, between about 0.15% and about 0.20%, preferably between about 0.16% and about 0.19%, more preferably between about 0.17% and about 0.19%, most preferably about 0.18% HIPMC, between about 0.5% and about 1.5%, between about 0.6% and about 1.4%, between about 0.7% and about 1.3%, between about 0.8% and about 1.4%, between about 0.9% and about 1.1%, and about 1% PEG-400, and water.

Embodiment 58. A pharmaceutically acceptable thermally gelling hydrogel consisting essentially of:

about 20% to about 35%, about 25% to about 30%, or about 27% of a poloxamer, preferably the poloxamer is Poloxamer 407, between about 0.15% and about 0.20%, preferably between about 0.16% and about 0.19%, more preferably between about 0.17% and about 0.19%, most preferably about 0.18% HIPMC, between about 0.5% and about 1.5%, between about 0.6% and about 1.4%, between about 0.7% and about 1.3%, between about 0.8% and about 1.4%, between about 0.9% and about 1.1%, and about 1% PEG-400, and water.

Embodiment 59. The pharmaceutically acceptable thermally gelling hydrogel of Embodiments 57 or 58, wherein no visible precipitation is observed in about 70 to about 100 mL of the pharmaceutically acceptable thermally gelling hydrogel during or after about 6 months of storage at about 40° C.

Embodiment 60. A thermally gelling pharmaceutical composition comprising:

about 1.33 mg/mL mitomycin C, about 20% to about 35%, about 25% to about 30%, or about 23% to about 25%, or about 27% of a poloxamer, preferably the poloxamer is Poloxamer 407, between about 0.15% and about 0.20%, between about 0.16% and about 0.19%, between about 0.17% and about 0.19%, about 0.16%, or about 0.18% HPMC, between about 0.5% and about 1.5%, between about 0.6% and about 1.4%, between about 0.7% and about 1.3%, between about 0.8% and about 1.4%, between about 0.9% and about 1.1%, and about 1% PEG-400, and water.

Embodiment 61. A thermally gelling pharmaceutical composition consisting essentially of:

1.33 mg/mL mitomycin C, about 20% to about 35%, about 25% to about 30%, or about 27%, or about 24.32% of a poloxamer, preferably the poloxamer is Poloxamer 407, between about 0.15% and 0.20%, between about 0.16% and 0.19%, between about 0.17% and 0.19%, or about 0.18% HPMC, between about 0.5% and about 1.5%, between about 0.6% and about 1.4%, between about 0.7% and about 1.3%, between about 0.8% and about 1.4%, between about 0.9% and about 1.1%, and about 1% PEG-400, and water.

Embodiment 62. The thermally gelling pharmaceutical composition of Embodiment 61, wherein the thermally gelling pharmaceutical composition has a volume of about 56 mL and comprises about 75 mg mitomycin C.

Embodiment 63. The thermally gelling pharmaceutical composition of any of Embodiments 60-62 for use in treatment of recurrent low grade intermediate risk non-muscle-invasive bladder cancer, wherein after administration about 56 mL of the thermally gelling pharmaceutical composition, once weekly for six weeks into the bladders of a population of patients suffering from recurrent low grade intermediate risk non-muscle-invasive bladder cancer, said population of patients exhibits at least a 50%, a 55%, a 60%, a 65%, a 70% or a 75% reduction in risk of recurrence, progression or death from recurrent low grade intermediate risk non-muscle-invasive bladder cancer at 6 months after treatment, and at least a 25%, a 30%, a 35% or a 40% reduction in risk of recurrence, progression or death from recurrent low grade intermediate risk non-muscle-invasive bladder cancer at one or more of 9, 12, and 15 months after treatment, relative to an otherwise equivalent population of patients suffering from recurrent low grade intermediate risk non-muscle-invasive bladder cancer who have been treated only with TURBT.

In an embodiment, a method of treating recurrent low grade intermediate risk non-muscle-invasive bladder cancer in a patient comprising administering into the bladder of the patient about 45 to about 85 ml of a thermally gelling mitomycin C composition comprising about 60-120 mg, or about 75 mg of mitomycin C.

In the a method of the above embodiment, said administering is carried out once weekly for six weeks.

Mitomycin C can be wetted with the thermally gelling hydrogel prior to said mixing.

The thermally gelling hydrogel can be diluted with water prior to said mixing.

The thermally gelling mitomycin C composition can be prepared within about 48 hours of said administering.

The thermally gelling mitomycin C composition can be stored at a temperature below about 8° C. prior to said administering.

The thermally gelling mitomycin C composition can be stored at a temperature ranging from about 2° C. to about 8° C. prior to said administering.

About 80 mg of mitomycin C can be mixed with about 60 ml of the thermally gelling hydrogel.

The volume of thermally gelling mitomycin C composition administered is preferably about 56 ml.

Administering thermally gelling mitomycin C composition to a patient is preferably performed following TURBT surgery.

The patient can have a single tumor or multifocal tumors.

A method of reducing bladder tumor recurrence, progression, or death in a population of patients suffering from recurrent low grade intermediate risk non-muscle-invasive bladder cancer, comprises administering into the bladder of each of the patients in the population 45-85 ml of a thermally gelling composition comprising 75 mg of mitomycin C, wherein at least a 50%, a 55%, a 60%, a 65%, a 70% or a 75% reduction in risk of recurrence, progression or death from recurrent low grade intermediate risk non-muscle-invasive bladder cancer at 6 months after treatment, and at least a 25%, a 30%, a 35% or a 40% reduction in risk of recurrence, progression or death from recurrent low grade intermediate risk non-muscle-invasive bladder cancer at one or more of 9, 12, and 15 months after administration of the thermally gelling composition compared to an otherwise equivalent population of patients suffering from recurrent low grade intermediate risk non-muscle-invasive bladder cancer who have received only TURBT therapy.

Said administering can be carried out once weekly for six weeks.

The thermally gelling mitomycin C composition can be prepared within 14 days of said administering by mixing mitomycin C together with a thermally gelling hydrogel, wherein said thermally gelling hydrogel comprises:

- about 20% to about 35%, about 25% to about 30%, or about 27% of a poloxamer, preferably the poloxamer is Poloxamer 407,
- between 0.15% and 0.20%, preferably between 0.16% and 0.19%, more preferably between 0.17% and 0.19%, most preferably about 0.18% HPMC,
- between 0.5% and 1.5%, between 0.6% and 1.4%, between 0.7% and 1.3%, between 0.8% and 1.4%, between 0.9% and 1.1%, and about 1% PEG-400, and
- water.

Mitomycin C can be wetted with the thermally gelling hydrogel prior to said mixing.

The thermally gelling hydrogel can be diluted with water prior to said mixing.

The thermally gelling mitomycin C composition can be prepared within 48 hours of said administering.

The thermally gelling mitomycin C composition can be stored at a temperature below about 8° C. prior to said administering.

The thermally gelling mitomycin C composition can be stored at a temperature ranging from about 2-8° C. prior to said administering.

About 80 mg of mitomycin C is mixed with 60 ml of the thermally gelling hydrogel.

The volume of thermally gelling mitomycin C composition administered is about 56 ml.

Said administering is preferably made to a patient following TURBT surgery.

The patient can have a single tumor or multifocal tumors.

A pharmaceutically acceptable thermally gelling hydrogel can comprise:

- about 20% to about 35%, about 25% to about 30%, or about 27% of a poloxamer, preferably the poloxamer is Poloxamer 407,
- between 0.15% and 0.20%, preferably between 0.16% and 0.19%, more preferably between 0.17% and 0.19%, most preferably about 0.18% HPMC,
- between 0.5% and 1.5%, between 0.6% and 1.4%, between 0.7% and 1.3%, between 0.8% and 1.4%, between 0.9% and 1.1%, and about 1% PEG-400, and
- water.

A pharmaceutically acceptable thermally gelling hydrogel can consist essentially of:

- about 20% to about 35%, about 25% to about 30%, or about 27% of a poloxamer, preferably the poloxamer is Poloxamer 407,
- between 0.15% and 0.20%, preferably between 0.16% and 0.19%, more preferably between 0.17% and 0.19%, most preferably about 0.18% HPMC,
- between 0.5% and 1.5%, between 0.6% and 1.4%, between 0.7% and 1.3%, between 0.8% and 1.4%, between 0.9% and 1.1%, and about 1% PEG-400, and
- water.

The pharmaceutically acceptable thermally gelling hydrogels described above can have no visible precipitation observed in 70-100 ml of the pharmaceutically acceptable thermally gelling hydrogel during or after 6 months of storage at 40° C.

In an embodiment, a thermally gelling pharmaceutical composition comprises:

- 1.33 g/ml mitomycin C,
- about 20% to about 35%, about 25% to about 30%, or about 27% of a poloxamer, preferably the poloxamer is Poloxamer 407,
- between 0.15% and 0.20%, preferably between 0.16% and 0.19%, more preferably between 0.17% and 0.19%, most preferably about 0.18% HPMC,
- between 0.5% and 1.5%, between 0.6% and 1.4%, between 0.7% and 1.3%, between 0.8% and 1.4%, between 0.9% and 1.1%, and about 1% PEG-400, and
- water.

In another embodiment, a thermally gelling pharmaceutical composition consists essentially of:

- 1.33 mg/ml mitomycin C,
- about 20% to about 35%, about 25% to about 30%, or about 27% of a poloxamer, preferably the poloxamer is Poloxamer 407,
- between 0.15% and 0.20%, preferably between 0.16% and 0.19%, more preferably between 0.17% and 0.19%, most preferably about 0.18% HPMC,
- between 0.5% and 1.5%, between 0.6% and 1.4%, between 0.7% and 1.3%, between 0.8% and 1.4%, between 0.9% and 1.1%, and about 1% PEG-400, and
- water.

The thermally gelling pharmaceutical composition described above can be prepared by mixing a sufficient volume of the pharmaceutically acceptable thermally gelling hydrogel of any of Embodiments 25-27 with sufficient mitomycin to provide about 45 to about 48 ml of the thermally gelling pharmaceutical composition.

The thermally gelling pharmaceutical composition can have a volume of about 56 ml and comprises about 75 mg mitomycin C.

In another embodiment, the thermally gelling pharmaceutical composition of any of thermally gelling pharmaceutical composition described above for use in treatment of recurrent low grade intermediate risk non-muscle-invasive bladder cancer, wherein after administering 56 ml of the thermally gelling pharmaceutical composition, once weekly for six weeks into the bladders of a population of patients suffering from recurrent low grade intermediate risk non-muscle-invasive bladder cancer, said population of patients exhibits at least a 50%, a 55%, a 60%, a 65%, a 70% or a 75% reduction in risk of recurrence, progression or death from recurrent low grade intermediate risk non-muscle-invasive bladder cancer at 6 months after treatment, and at least a 25%, a 30%, a 35% or a 40% reduction in risk of recurrence, progression or death from recurrent low grade intermediate risk non-muscle-invasive bladder cancer at one or more of 9, 12, and 15 months after treatment, relative to an otherwise equivalent population of patients suffering from recurrent low grade intermediate risk non-muscle-invasive bladder cancer who have been treated only with TURBT.

These examples are provided for the purpose of further illustration only and are not intended to be limitations on the disclosure.

EXAMPLES

Phase 2b, Open-Label, Single-Arm Trial for Primary Chemoablation of Low-Grade Intermediate-Risk Non-Muscle-Invasive Bladder Cancer Using UGN-102, a Mitomycin-Containing Reverse Thermal Gel (OPTIMA II)

Study Design and Population

A phase 2b, open-label, single-arm trial was conducted from Oct. 15, 2018, to Oct. 21, 2020, at 20 sites in the U.S. and Israel. Eligible patients were ≥18 years old with LG NMIBC (Ta) diagnosed using cold cup biopsy (with visible tumor left in situ) and negative voiding cytology for high-grade (HG) disease within 6 weeks before screening. IR disease was defined as having 1 or 2 of the following: presence of multiple tumors, solitary tumor >3 cm and/or recurrence (≥1 occurrence of LG NMIBC within 1 year of the current diagnosis). Patients were required to have adequate organ and bone marrow function as determined by routine laboratory testing (leukocytes ≥3,000 cells per µl, absolute neutrophil count ≥1,500 cells per µl, platelets ≥100,000 per µl, hemoglobin ≥9.0 gm/dl, total bilirubin ≤1.5×upper limit of normal, aspartate aminotransferase, alanine aminotransferase, and alkaline phosphatase ≤2.5× upper limit of normal and estimated glomerular filtration rate ≥30 ml/min). Patients with past or present muscle-invasive or metastatic urothelial carcinoma (UC), concurrent upper tract UC (UTUC) and patients with a history of carcinoma in situ within the previous 5 years, HG papillary UC within the previous 2 years or those who had received *bacillus* Calmette-Guerin treatment for UC within the previous 2 years were excluded.

All patients provided written informed consent before initiating any study-related procedure. The trial protocol, amendments and informed consent form were approved by the institutional review board at each participating site (IRB No. TC-BC-12). The trial was conducted in compliance with the Declaration of Helsinki, International Council for Harmonization guidelines and the U.S. Code of Federal Regulations Title 21, parts 50, 56 and 312. The study is registered with ClinicalTrials.gov (NCT03558503).

Procedures

Eligible patients received 6 once-weekly intravesical instillations of UGN-102 (75 mg mitomycin in 56 ml admixture with reverse thermal hydrogel to equal 1.33 mg/ml). In the event of a urinary tract infection or another safety reason (e.g., inadequate organ function), treatment could be postponed for up to 4 weeks until the event resolved. The ablative effect of UGN-102 was evaluated at the 3-month visit, which occurred 4 to 6 weeks after the last weekly instillation and 3 months after treatment initiation. Response was determined based on visual assessment (cystoscopy), biopsy of remaining lesions (if applicable) and voided urine cytology. If cystoscopy indicated no remaining tumors and urine cytology was negative, the patient had no detectable disease and was considered a complete response (CR). If the bladder was free of tumor endoscopically but cytology was positive, the investigator was required to exclude UTUC and occult carcinoma of the bladder or urethra. If UTUC was confirmed, the patient was considered to have CR. If any lesions were detected, even if they appeared necrotic, a biopsy was taken from the suspect tissue. If the biopsy was negative for cancer, the case was considered CR, and if the biopsy was positive, the case was considered non-CR. Patients who achieved CR continued to have monthly telephone contacts to document any adverse events (AEs) and were assessed for evidence of disease recurrence at 6, 9 and 12 months after the first instillation of UGN-102. Patients considered non-CR discontinued the study and continued with standard of care therapy as determined by their treating physicians.

Outcomes

The primary efficacy end point was CR rate, defined as the percentage of patients with CR at the 3-month visit. The secondary efficacy end point was durable CR in patients who achieved CR at the 3-month visit, defined as the percentage of patients with no detectable disease at 6, 9 and 12 months after treatment initiation. In addition to the durable CR rate, the duration of CR was defined as time from the date of evidence of CR at the 3-month visit to the earliest date of recurrence as determined using the date of cystoscopy, biopsy or cytology, whichever occurred first.

Safety was assessed throughout the study. AEs were coded using the Medical Dictionary for Regulatory Activities (MedDRA) version 21.0 and graded according to the National Cancer Institute Common Terminology Criteria for Adverse Events (CTCAE) version 5.0.

Statistical Analysis

SAS® software was used to perform all data analyses. Sample size was determined based on an expectation that 60% of patients would achieve CR. Assuming a 10% drop-out rate, approximately 66 patients were to be recruited to provide adequate power to establish that the observed CR rate was superior to 45%. The primary analysis was performed using all patients who received at least 1 instillation of UGN-102 (intent-to-treat [ITT] analysis set). A test for binomial proportions was used to derive the exact 2-sided 95% CI for the CR rate using the Clopper-Pearson method.

Subgroup analyses of the primary end point, including frequency and percentage of CR and exact 95% CIs, were conducted for descriptive purposes.

Point estimates and 2-sided exact 95% binomial CIs (Clopper-Pearson method) for durable CR rate at 6, 9 and 12 months after treatment initiation were summarized using all patients who achieved CR at the 3-month visit (3-month CR analysis set). Duration of CR was estimated using the Kaplan-Meier method. If a patient did not have a recurrence, the patient was censored at the date of the last adequate disease assessment or date of death.

Analyses of AEs were performed using the ITT analysis set, which was identical to the safety analysis set. Treatment-emergent AEs (TEAEs) reported for ≥3 patients were summarized descriptively by preferred term and maximal severity.

Results

A total of 63 patients were enrolled in the trial and treated with ≥1 instillation of UGN-102 (FIG. 1). Of these patients 57 (90%) completed 6 instillations of UGN-102 according to protocol and 6 patients discontinued treatment due to an AE. Median age was 68.0 years (range 33-96), 57% of patients were ≥65 years old and 40% of patients were ≥75 years old (table 1). Most patients were male (60%) and Caucasian (87%). A total of 49 patients (78%) had recurrent LG NMIBC and 28 (44%) had a previous episode within 1 year of the current diagnosis. Patients with recurrence underwent a median of 3.0 prior TURBTs (range 0-13), with 37 (76%) having ≥2 prior TURBTs and 28 (57%) having ≥3 prior TURBTs. Among patients with data available, 50/61 (82%) had multiple visible tumors and 17/61 (28%) had tumors >3 cm.

TABLE 1

Patient characteristics (ITT analysis set).

| Characteristic | All Treated Pts (63) | |
|---|---|---|
| Age (yrs): | | |
| Mean (SD) | 70.5 | (11.7) |
| Median (range) | 68.0 | (33.0-96.0) |
| No. age group (%): | | |
| <65 yrs | 27 | (42.9) |
| 65 to <75 yrs | 11 | (17.5) |
| ≥75 yrs | 25 | (39.7) |
| No. gender (%): | | |
| Male | 38 | (60.3) |
| Female | 25 | (39.7) |
| No. race: | | |
| Caucasian | 55 | (87.3) |
| Asian | 3 | (4.8) |
| Hispanic | 3 | (4.8) |
| African American | 1 | (1.6) |
| Other | 1 | (1.6) |
| No. tumor size (%):* | | |
| ≤3 cm | 44 | (72.1) |
| >3 cm | 17 | (27.9) |
| No. tumors (%):* | | |
| Single | 11 | (18.0) |
| Multiple | 50 | (82.0) |
| No. visual appearance of lesions (%): | | |
| Papillary | 63 | (100.0) |
| Flat | 2 | (3.2) |
| Other | 2 | (3.2) |
| No. tumor staging (%): | | |
| Noninvasive papillary Ca | 62 | (98.4) |
| Other† | 2 | (3.2) |
| No. tumor grading (%): | | |
| Papillary urothelial Ca, LG | 62 | (98.4) |
| Papillary urothelial neoplasm of low malignant potential | 1 | (1.6) |
| Other | 2 | (3.2) |
| No. any previous LG NMIBC episode (%) | 49 | (77.8) |
| No. previous LG NMIBC episode within 1 yr of current diagnosis (%) | 28 | (44.4) |
| No. prior TURBTs: ‡ | | |
| Mean (SD) | 4.0 | (3.3) |
| Median (range) | 3.0 | (0.0-13.0) |
| No. prior TURBTs (%):‡ | | |
| 0 | 2 | (4.1) |
| 1 | 10 | (20.4) |
| 2 | 9 | (18.4) |
| ≥3 | 28 | (57.1) |
| Days since last TURBT at day 1 (%):§ | | |
| ≤365 | 23 | (48.9) |
| >365 | 24 | (51.1) |

A patient may have more than 1 result for classification of tumor staging, grading and visual appearance of lesions.
*Measured in 61 patients.
†Staging was reported as "noninvasive papillary carcinoma (Ta)" and "sessile but LG" for 1 patient, and as "papillary urothelial carcinoma, low-grade, no extension into lamina propria identified, muscularis propria not sampled" for 1 patient.
‡Measured in 49 patients
§Measured in 47 patients.

Figure 2:
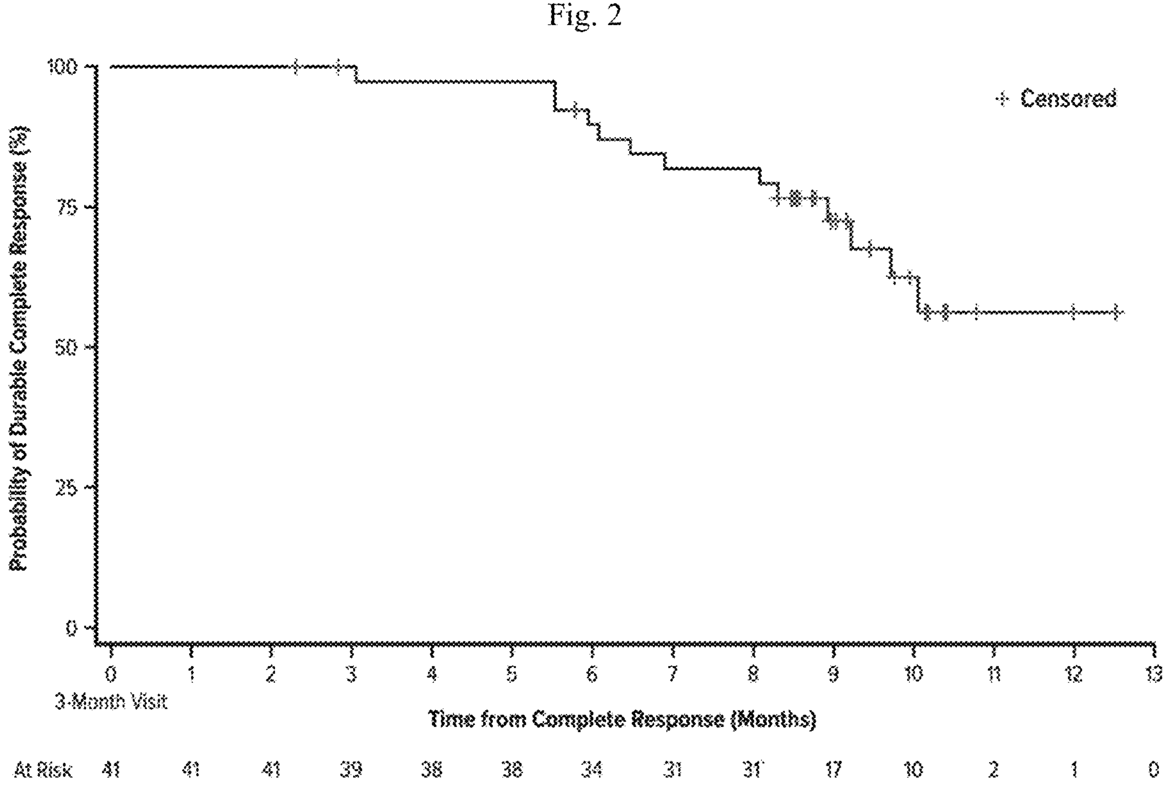
FIG. 2 is a Kaplan-Meier plot of duration of CR (3-month CR analysis set) for the OPTIMA II study.

A total of 41 patients (65%) achieved CR at 3 months after treatment initiation (95% CI 52.0, 76.7). See Table 2. Among 22 patients who were non-CR, 20 showed evidence of persistence or worsening of disease, including 5 who had HG papillary UC and/or UC in situ, suggesting under grading at the time of diagnosis. Of the 41 patients with CR, 39 (95%), 30 (73%) and 25 (61%) remained free of disease at 6, 9 and 12 months after treatment initiation, respectively. See Table 3. A total of 13 patients (32%) had disease recurrence (2 of whom were determined to have a more aggressive tumor than diagnosed at screening, which was considered evidence of disease progression), and 3 patients terminated the study early: 1 due to an AE, 1 due to death, and 1 patient was unable to complete the study due to concerns about COVID-19. The median duration of response (DOR) was not estimable. See FIG. 2. However, the probability of durable response 9 months after CR (12 months after treatment initiation) estimated by the Kaplan-Meier method was 72.5% (95% CI 54.4, 84.3).

TABLE 2

Complete response at 3-month visit (ITT analysis set).

| | All Treated Pts (63) | |
|---|---|---|
| | No. (%)* | Exact 95% CI† |
| Complete response | 41 (65.1) | (52.0, 76.7) |
| Noncomplete response | 22 (34.9) | |

TABLE 2-continued

Complete response at 3-month visit (ITT analysis set).

| | All Treated Pts (63) | |
|---|---|---|
| | No. (%)* | Exact 95% CI† |
| Evidence of persistence/ worsening of disease‡ | 20 (31.7) | |
| Indeterminate | 2 (3.2) | |

*Percentages are computed using total number as denominator.
†Exact 95% CI for CR rate is computed using Clopper-Pearson method.
‡Five patients were determined by investigator to have HG papillary urothelial carcinoma and/or UC in situ at 3-month visit. Given that all 5 patients were determined by investigator to have LG papillary UC at screening, these cases likely represent under staging/under grading at time of diagnosis rather than true disease progression.

TABLE 3

Durability of complete response (3-month CR analysis set).

| | Durable Complete Response Rate | | | |
|---|---|---|---|---|
| Time Point* | No./N1 (%)† | Exact 95% CI‡ | No./N2 (%)§ | Exact 95% CI‡ |
| 6 mos (3 mos after CR at 3-month visit) | 39/41 (95.1) | (83.5, 99.4) | 39/40 (97.5) | (86.8, 99.9) |
| 9 mos (6 mos after CR at 3-month visit) | 30/41 (73.2) | (57.1, 85.8) | 30/39 (76.9) | (60.7, 88.9) |
| 12 mos (9 mos after CR at 3-month visit) | 25/41 (61.0) | (44.5, 75.8) | 25/38 (65.8) | (48.6, 80.4) |

N1, number of patients who achieved CR at 3-month visit; N2, number of evaluable patients who reached followup visit with durable CR or evidence of disease recurrence.
*Time points of 6, 9 and 12 months are relative to start of study treatment.
†Percentages are computed using N1 as denominator (ie all patients in 3-month CR analysis set are included in denominator for computing durable CR rate).
‡Exact 95% CIs for durable CR rates are computed using Clopper-Pearson method.
§Percentages are computed using N2 as denominator (ie evaluable patients who terminated study early or patients who had indeterminate response are excluded from denominator for computing durable CR rate).

Overall, 57 of 63 patients (90%) experienced TEAEs and 40 (63%) had TEAEs that were considered related to study drug or procedure. Five patients (8%) had ≥1 serious TEAE, none of which was considered related to study drug or procedure. One patient experienced 4 serious TEAEs (cardiac disorder, hematuria, pneumonia and *Klebsiella pneumonia*), 1 patient experienced 2 serious TEAEs (chronic obstructive pulmonary disease and stress cardiomyopathy) and 3 patients each experienced 1 serious TEAE (acute myeloid leukemia, gastroenteropancreatic neuroendocrine tumor disease and metastatic urothelial carcinoma). The event of acute myeloid leukemia was life-threatening, and the event of cardiac disorder in a 91-year-old male resulted in death. See Table 4. The event of metastatic UC likely represents invasive or HG disease not diagnosed at screening. Computerized tomography 6 months after the last study treatment revealed extensive lymph node spread. The location of primary cancer was unconfirmed but suspected to be the bladder. Cystoscopy and cytology were negative from the 3-month visit through end of study. Six patients (10%) had ≥1 TEAE leading to treatment discontinuation, all of which were considered related to study drug or procedure. One patient experienced 3 TEAEs leading to treatment discontinuation (dysuria, micturition urgency and penile erythema), and 5 patients each experienced 1 TEAE leading to treatment discontinuation (lower urinary tract symptoms in 2, hand dermatitis in 1, generalized rash in 1 and urinary retention in 1).

TABLE 4

TEAEs reported in ≥3 patients by preferred term and maximum severity (ITT analysis set).

| TEAE Preferred | No. Treated Pts (%) | | | |
|---|---|---|---|---|
| Term | Grades 1-2* | Grade 3† | Grade 4‡ | Grade 5§ |
| Pts with any TEAE | 50 (79.4) | 5 (7.9) | 1 (1.6) | 1 (1.6) |
| Dysuria | 26 (41.3) | 0 | 0 | 0 |
| Pollakiuria | 13 (20.6) | 0 | 0 | 0 |
| Hematuria | 9 (14.3) | 1 (1.6) | 0 | 0 |
| Micturition urgency | 9 (14.3) | 0 | 0 | 0 |
| Urinary tract infection | 9 (14.3) | 0 | 0 | 0 |
| Fatigue | 7 (11.1) | 0 | 0 | 0 |
| Urinary incontinence | 5 (7.9) | 0 | 0 | 0 |
| Accidental exposure to product | 4 (6.3) | 0 | 0 | 0 |
| Nocturia | 4 (6.3) | 0 | 0 | 0 |
| Pruritus genital | 4 (6.3) | 0 | 0 | 0 |
| Urinary retention | 4 (6.3) | 0 | 0 | 0 |
| Vulvovaginal discomfort | 4 (6.3) | 0 | 0 | 0 |
| Bladder spasm | 3 (4.8) | 0 | 0 | 0 |
| Constipation | 3 (4.8) | 0 | 0 | 0 |
| Genital discomfort | 3 (4.8) | 0 | 0 | 0 |
| Lower urinary tract symptoms | 3 (4.8) | 0 | 0 | 0 |
| Penile edema | 2 (3.2) | 1 (1.6) | 0 | 0 |
| Rash generalized | 3 (4.8) | 0 | 0 | 0 |
| Sinusitis | 3 (4.8) | 0 | 0 | 0 |

Total of 63 patients were treated.
Percentages are computed using total number treated as denominator. Patients with more than 1 episode of same AE are counted only once (under worst severity category).
*Severity grades are defined as 1, mild; 2, moderate; 3, severe or medically significant; 4, life-threatening; 5, fatal.
†Other grade 3 events were arthralgia, chronic obstructive pulmonary disease, gastroenteropancreatic neuroendocrine tumor disease, Klebsiella pneumonia and metastatic urothelial carcinoma, each occurring in 1 patient.
‡Grade 4 event was acute myeloid leukemia, which was not related to study drug or procedure.
§Cause of death (grade 5 event) was cardiac disorder (reported term: exacerbation of chronic heart disease), which was not related to study drug or procedure.

Adverse events of special interest (AESIs) occurred in 44 of 63 (69.8%) of patients. The most frequently reported TEAEs were dysuria in 26 of 63 patients (41%), urinary frequency in 13 (21), hematuria in 10 (160), micturition urgency and urinary tract infection in 9 (140%), and fatigue in 7 (110%). Regarding TEAEs of special interest (i.e., lower urinary tract symptoms, allergic reactions, voiding interruption due to urethral/penile edema, genitourinary infections, inadvertent or accidental exposure to UGN-102 and bone marrow suppression), 43 of 44 patients (980) had events that were mild or moderate in severity and 35 (800%) had events that resolved during the study. Among the 9 cases with TEALs of special interest that did not resolve, 6 events were considered not related to study drug or procedure.

TABLE 5

Participants with Post-baseline Potentially Clinically Significant (PCS) Findings.

| Finding | No. (%) |
|---|---|
| Any PCS chemistry value | 8 (12.7) |
| Any PCS hematology value | 4 (6.3) |
| Any PCS vital signs | 8 (12.7) |

TABLE 5-continued

| Participants with Post-baseline Potentially Clinically Significant (PCS) Findings. | |
|---|---|
| Finding | No. (%) |
| Any abnormal, CS physical examination findings | 0 (0.0) |
| CS urology-oriented physical examination findings | 2 (3.2) |

TABLE 6

Mitomycin plasma concentrations for 6 patients.

| Time | Mean (standard deviation) ng/mL | Concentration-time Curve (AUC) - Mean (standard deviation) ng/mL (0-6 hours after first instillation) | Concentration (Cmax) |
|---|---|---|---|
| Pre-instillation | 0 | 5.69 (7.30) | 2.27 (3.33) |
| 0.5 hour post-instillation | 0.75 (0.57) | | |
| 1 hour post-instillation | 0.60 (0.42) | | |
| 2 hours post-instillation | 0.34 (0.17) | | |
| 3 hours post-instillation | 1.88 (3.13) | | |
| 4 hours post-instillation | 1.93 (3.49) | | |
| 5 hours post-instillation | 0.57 (0.61) | | |
| 6 hours post-instillation | 0.32 (0.32) | | |

Discussion

In the current study, 63 patients with biopsy-proven LG IR NMIBC received induction chemoablative therapy with UGN-102 and 41 (65%) achieved CR at 3 months after treatment initiation. Of these 41 patients 25 (61%) remained disease-free 9 months after achieving CR (12 months after treatment initiation). Among the 41 patients who initially achieved CR, 13 had documented disease recurrence during follow-up, including 2 patients whose tumors were determined to be more aggressive than diagnosed at screening and thus evidenced disease progression. The probability of durable response was estimated to be 72.5% by Kaplan-Meier analysis. The median duration of response was not reached. Treatment with UGN-102 was generally well-tolerated. AEs were primarily mild or moderate in severity, and no study drug or procedure-related serious TEAEs were reported.

Conclusions

Nonsurgical primary chemoablation of LG IR NMIBC using UGN-102 results in a clinically significant treatment response with demonstrated durability. UGN-102 may provide an alternative to repetitive TURBT surgery for patients with LG IR NMIBC.

Phase 3 Study of UGN-102 for Low-Grade Intermediate-Risk Non-Muscle Invasive Bladder Cancer (ATLAS)

Study Design and Population

Figure 3:
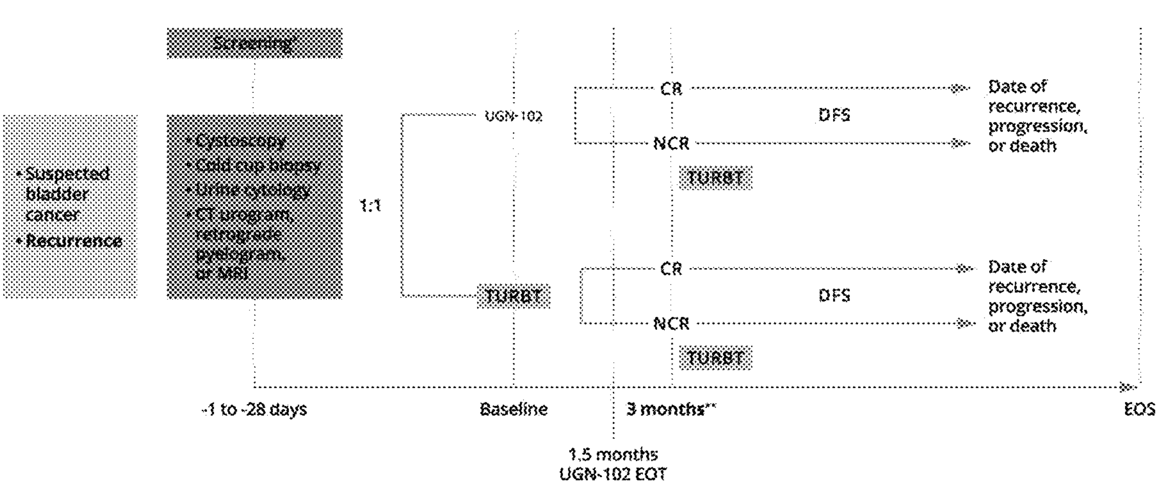
FIG. 3 is a flow diagram of the study design of the ATLAS study.

A phase 3, open-label, prospective, randomized, controlled study to assess efficacy and safety of UGN-102 for intravesical instillation with or without subsequent TURBT vs. TURBT alone in the treatment of patients with LG IR NMIBC was conducted from Jan. 12, 2021, to Mar. 17, 2023, at 72 sites in the U.S., Europe, and Israel. Eligible patients were ≥18 years of age with LG NMIBC (Ta) diagnosed using cold cup biopsy (with visible tumor left in situ) and negative voiding cytology for high-grade (HG) disease. IR disease was defined as having 1 or 2 of the following: presence of multiple tumors, solitary tumor >3 cm, and/or recurrence of LG NMIBC within 1 year of the current diagnosis. Eligible patients were randomized in a 1:1 ratio to UGN-102 with or without TURBT or TURBT alone. See FIG. 3, Study Design, where CT=computed tomography; EOS=end of study; EOT=end of treatment; and MRI=magnetic resonance imaging. Patients randomized to the UGN-102 group received 6 weekly intravesical instillations followed by diagnostic cystoscopy (with TURBT only if needed) and patients randomized to the TURBT alone group received TURBT followed by diagnostic cystoscopy (with repeat TURBT if needed). Disease-free survival (DFS) was the primary endpoint.

All patients were scheduled to return to the clinic approximately 3 months after start of treatment for determination of response. Patients confirmed to have complete response (CR) received no further treatment and entered the follow-up period of the study. Patients confirmed to have non-complete response (NCR) in either treatment arm were treated by TURBT for any remaining lesions and then entered the follow-up period. During the follow-up period, patients were scheduled to return to the clinic quarterly, and patients determined to be disease-free remained on study until completion of all follow-up visits (≥15 months after start of treatment) or until disease recurrence, disease progression, or death was documented. Patients determined to have had a protocol-defined recurrence or progression at any follow-up or unscheduled visit were considered to have completed the study and were released to the care of their treating physicians.

The trial protocol, amendments, and informed consent form were approved by the institutional review board at each participating site (IRB No. BL006). The trial was conducted in compliance with the Declaration of Helsinki, International Council for Harmonization guidelines, and the U.S. Code of Federal Regulations Title 21, parts 50, 56 and 312. The study is registered with ClinicalTrials.gov (NCT04688931).

Procedures

Eligible patients received either 6 once-weekly intravesical instillations of UGN-102 (75 mg mitomycin in 56 mL admixture with reverse thermal hydrogel to equal 1.33 mg/mL) or TURBT. Patients randomized to TURBT did not receive adjuvant immunotherapy or chemotherapy in an effort to mimic contemporary practice. The ablative effect of UGN-102 or TURBT was evaluated 3 months after start of treatment. Response was determined based on visual assessment (cystoscopy), biopsy of remaining lesions (if applicable), and voided urine cytology. If cystoscopy indicated no remaining tumors and urine cytology was negative, the patient had no detectable disease and was considered CR. If the bladder was free of tumor endoscopically but cytology was positive, the investigator was required to exclude upper tract urothelial carcinoma (UTUC) and occult carcinoma of the bladder or urethra. If any lesions were detected, even if they appeared necrotic, a biopsy was taken for further evaluation.

Outcomes

The primary efficacy endpoint of DFS was defined as the time from randomization until treatment failure or death from any cause. Treatment failure comprised residual LG disease at the 3-month assessment (TURBT arm only), recurrence of LG disease at any time after the 3-month assessment, or progression to HG disease at any time. Residual LG disease at the 3-month assessment in the UGN-102±TURBT treatment arm was not counted as a DFS event since such an outcome would not be considered treatment failure following neoadjuvant therapy. DFS was analyzed based on the intent to treat (ITT) population, defined as all patients who were randomized to treatment. Key secondary endpoints included CR rate and duration of response (DOR). Treatment effects on disease-related symptoms, functioning, and health-related quality of life were assessed using the European Organisation for Research and Treatment of Cancer Quality of Life Questionnaire for Non-muscle Invasive Bladder Cancer patients (EORTC-QLQ-NMIBC24). Blazeby, et al., Eur Urol. 2014; 66(6): 1148-1156.

The safety population comprised all patients who received ≥1 instillation of UGN-102 or underwent primary TURBT. Adverse events were assessed via verbal questioning during study visits or (for the TURBT alone arm) telephone follow-up and were coded using the Medical Dictionary for Regulatory Activities (MedDRA) version 23.1, graded according to the National Cancer Institute Common Terminology Criteria for Adverse Events (CTCAE) version 5.0.

Statistical Analysis

The trial was designed with a target sample size of 632 patients to observe an estimated 470 DFS events which would provide 80% power to detect a hazard ratio of 0.77 in the UGN-102 group as compared to the TURBT group, using a one-sided log-rank test at a significance level of 0.025. The hazard ratio was based on an assumed median DFS of 12 months for the TURBT alone arm and 15.6 months for the UGN-102 arm.

A stratified log-rank test was planned for testing superiority of the UGN-102 arm compared to the TURBT alone arm for DFS. A stratified Cox regression model was used to estimate the hazard ratio of DFS, along with 95% confidence intervals (CIs). Patients who did not have a DFS event were censored at the date of last adequate disease assessment. The distribution function of DFS was estimated using the Kaplan-Meier method. Similar time-to-event statistical methodology was used for the secondary endpoint of DOR. The secondary endpoint of 3-month CR rate was summarized along with nominal 95% exact CI using the Clopper-Pearson method. A mixed effect model for repeated measures was planned to evaluate changes in the EORTC-QLQ-NMIBC24 measures. SAS software was used to perform all data analyses.

Study enrollment was terminated early by the sponsor to pursue an alternative development strategy for UGN-102 in the treatment of bladder cancer. Patients who had consented at the time the trial terminated were permitted to continue until end of study; the study was terminated after the last patient reached the 15-month visit. Early termination rendered the trial underpowered to perform hypothesis testing. Thus, all analyses are descriptive.

Results

A total of 282 patients were enrolled in the trial and randomized to receive UGN-102±TURBT (n=142) or to undergo primary TURBT (n=140), representing the ITT analysis set (FIG. 4, Patient Flow Diagram). The safety analysis set comprised 138 patients who received ≥1 dose of UGN-102 in the primary chemoablation treatment arm and 132 patients who were treated by primary TURBT. Of those treated with UGN-102, 132 patients (96%) completed 6 instillations; 5 (3.6%) discontinued treatment due to adverse events, and 1 (0.7%) discontinued due to violation of entry criteria. Most participants were ≥65 years and male in both study arms. The median age was 68 years in the UGN-102 arm and 67 years in the TURBT arm. Fifty-four patients (38%) randomized to the UGN-102 arm and 65 patients (46%) in the surgery arm had prior history of LG NMIBC, and 41 patients (29%) in the UGN-102 group and 40 patients (29%) in the TURBT group had prior history of LG NMIBC within 1 year of study entry. Fifty-two patients (37%) in the UGN-102 arm had prior TURBT compared with 64 patients (46%) in the TURBT arm. Multifocal tumor was identified at baseline in 82 patients (580%) randomized to the UGN-102 arm and 94 surgery patients (670%). Tumors >3 cm were identified in 67 UGN-102 patients (47%) and 59 surgery patients (420%). See Table 7.

TABLE 7

Baseline demographic and clinical characteristics (ITT analysis set).

| Characteristic | UGN-102 ± TURBT[a] (N = 142) | TURBT Alone (N = 140) |
|---|---|---|
| Age (years) | | |
| Mean (SD) | 66.7 (10.6) | 66.3 (10.5) |
| Median (range) | 68.0 (23-85) | 67.0 (29-88) |
| Age group, n (%) | | |
| ≥65 years | 91 (64) | 77 (55) |

TABLE 7-continued

Baseline demographic and clinical characteristics (ITT analysis set).

| Characteristic | UGN-102 ± TURBT[a] (N = 142) | TURBT Alone (N = 140) |
| --- | --- | --- |
| Sex, n (%) | | |
| Male | 105 (74) | 93 (66) |
| Race, n (%) | | |
| White | 140 (99) | 139 (99) |
| Ethnicity, n (%) | | |
| Not Hispanic or Latino | 140 (99) | 137 (98) |
| Body mass index (kg/m$^2$) | | |
| Mean (SD) | 27.8 (5.0) | 27.3 (4.7) |
| Median (range) | 26.9 (18.2-47.0) | 26.7 (17.3-41.9) |
| Tumor size,† n (%) | | |
| >3 cm | 67 (47) | 59 (42) |
| Tumor number,‡ n (%) | | |
| Multiple | 82 (58) | 94 (67) |
| Any previous LG NMIBC episode, n (%) | | |
| Yes | 54 (38) | 65 (46) |
| Previous LG NMIBC episode within 1 year of current diagnosis, n (%) | | |
| Yes | 41 (29) | 40 (29) |
| Prior TURBT, n (%) | | |
| Yes | 52 (37) | 64 (46) |
| Smoking history, n (%) | | |
| Yes | 79 (56) | 67 (48) |

[a]Patients randomized to initial treatment with UGN-102 were eligible to be treated with TURBT if NCR at 3 months with residual LG NMIBC.
†Measured in 136 patients in UGN-102 ± TURBT arm and 132 patients in TURBT Alone arm.
‡Measured in 136 patients in UGN-102 ± TURBT arm and 134 patients in TURBT Alone arm.

At the first disease assessment 3 months after start of treatment, CR was achieved by 92 UGN-102 patients (65% [95% C n 56.3, 72.6]) and 89 TURBT patients (64% [95% CI: 55.0, 71.5]) (Table 8). Disease progression was noted in 12 UGN-102 patients (8.5%) and 9 surgery patients (6.40%).

TABLE 8

Complete response rates at the 3-month visit following treatment (ITT analysis set).

| | UGN-102 ± TURBT[a] (N = 142) | TURBT Alone (N = 140) |
| --- | --- | --- |
| | n (%) [95% CI]† | n (%) [95% CI]† |
| Complete Response | 92 (65) [56.3, 72.6] | 89 (64) [55.0, 71.5] |
| Non-complete Response | n (%) | n (%) |
| All NCR | 50 (35) | 51 (36) |
| Residual Disease | 26 (18) | 22 (16) |
| Progression to High Grade Disease | 12 (8.5) | 9 (6.4) |
| Indeterminate | 3 (2.1) | 0 |
| Missing[b] | 9 (6.3) | 20 (14) |

[a]Patients randomized to initial treatment with UGN-102 were eligible to be treated with TURBT if NCR at 3 months with residual LG NMIBC.
[b]Of the 9 patients with a missing 3-month disease assessment in the UGN-102 ± TURBT arm, 4 were randomized but not treated, 2 discontinued due to adverse events, and 1 patient each violated entry criteria (did not have IR disease), withdrew consent, or sought treatment at another medical center. Of the 20 patients with a missing 3-month disease assessment in the TURBT Alone arm, 8 were randomized but not treated, 5 violated entry criteria (e.g., had T1 or HG Ta disease), 4 withdrew consent, and 1 patient each discontinued due to investigator discretion, noncompliance, or lost to follow-up.
†Exact 95% CI for CR rate was computed using the Clopper-Pearson method.

Among patients with residual LG disease at the 3-month assessment, 24/26 treated with UGN-102 and 18/22 treated with primary TURBT underwent TURBT.

Figure 5:
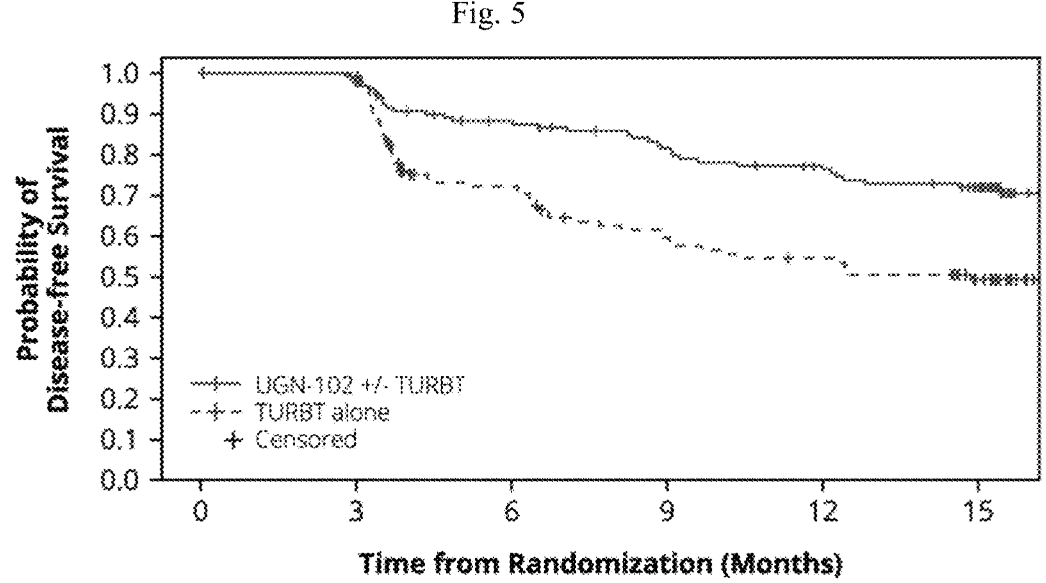
FIG. 5 shows Kaplan-Meier estimates of disease-free survival (intent-to-treat analysis set) in the ATLAS study.

DFS 15 months after randomization was estimated to be 72% (63%, 79%) for patients in the UGN-102±TURBT arm and 5000 (4000, 590%) for patients in the TURBT monotherapy arm by Kaplan-Meier analysis (FIG. 5 and Table 9).

TABLE 9

Kaplan-Meier estimates of disease-free survival.

| | Time from Randomization (months) | | | | | |
|---|---|---|---|---|---|---|
| | 0 | 3 | 6 | 9 | 12 | 15 |
| Kaplan-Meier estimates | | | | | | |
| UGN-102 +/− TURBT | 100% | 98% | 88% | 82% | 76% | 72% |
| TURBT alone | 100% | 99% | 72% | 60% | 55% | 50% |
| Number at risk | | | | | | |
| UGN-102 +/− TURBT | 142 | 128 | 108 | 96 | 87 | 73 |
| TURBT alone | 140 | 119 | 76 | 60 | 54 | 42 |
| Number censored | | | | | | |
| UGN-102 +/− TURBT | 0 | 11 | 19 | 23 | 26 | 35 |
| TURBT alone | 0 | 20 | 32 | 35 | 36 | 43 |

Figure 6:
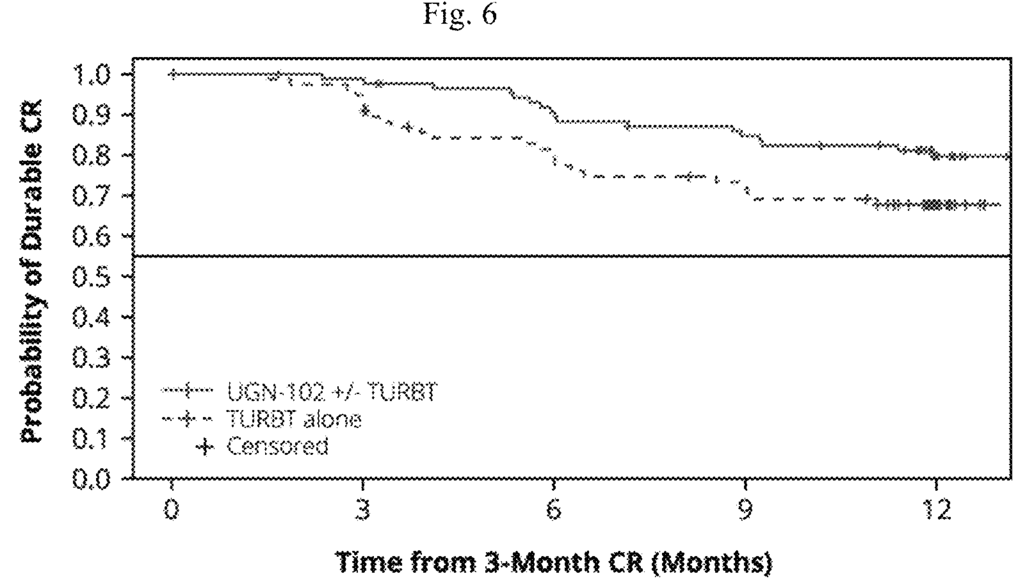
FIG. 6 shows Kaplan-Meier estimates of duration of response (3-month complete response analysis set) in the ATLAS study.

For the 92 patients achieving CR at 3 months after induction treatment with UGN-102, estimated DOR at 12 months post-CR was 79.700 (69.3%, 86.90%) compared with 67.7% (55.8%, 77.10%) for the 89 patients treated by primary TURBT who achieved CR (FIG. 6 and Table 10).

TABLE 10

Kaplan-Meier estimates of duration of response.

| | Time from 3-month CR (months) | | | | |
|---|---|---|---|---|---|
| | 0 | 3 | 6 | 9 | 12 |
| Kaplan-Meier estimates | | | | | |
| UGN-102 +/− TURBT | 100% | 99% | 91% | 85% | 80% |
| TURBT alone | 100% | 95% | 82% | 73% | 68% |
| Number at risk | | | | | |
| UGN-102 +/− TURBT | 92 | 86 | 77 | 71 | 49 |
| TURBT alone | 89 | 73 | 60 | 53 | 34 |
| Number censored | | | | | |
| UGN-102 +/− TURBT | 0 | 5 | 7 | 8 | 26 |
| TURBT alone | 0 | 12 | 15 | 16 | 31 |

Overall hazard ratios for DFS and DOR were 0.45 and 0.46, respectively. Among patients who were CR at the 3-month assessment, 66 (71.7%) treated with UGN-102 remained disease-free at month 15 compared with 49 (55%) of those treated initially with TURBT. Both UGN-102±TURBT and TURBT monotherapy were associated with improvements in urinary symptoms and intravesical treatment issues as measured by changes from baseline in the EORTC-QLQ-NMIBC24.

Treatment-emergent adverse events (TEAEs) occurred more commonly in patients treated with UGN-102 (75% v 48%). Fifty-four patients (39%) in the UGN-102±TURBT arm and 15 (11%) in the TURBT monotherapy arm experienced TEAEs related to study treatment. Serious TEAEs occurred in 12 patients (8.7%) who received UGN-102 and 7 patients (5.3%) in the surgery arm; however, no serious TEAEs in the UGN-102 group and one in the TURBT monotherapy group (post-operative hematuria) were considered by the investigator to be related to treatment. Treatment discontinuation and study discontinuation due to adverse events occurred in 5 (3.6%) and 4 (2.9%) patients receiving UGN-102. The most commonly reported adverse events in the UGN-102±TURBT arm of the study were dysuria (30%), micturition urgency (18%), nocturia (18%), and pollakiuria (16%). See Table 11. One death occurred during the study (in the TURBT arm) which was attributed to infection with COVID-19. Patient reported symptoms, functioning, and quality-of-life-as measured by changes from baseline in the EORTC-QLQ-NMIBC24-either were improved or not worsened in those treated with UGN-102±TURBT or TURBT alone.

TABLE 11

Summary of treatment-emergent adverse events (safety analysis set).

| | UGN-102 ± TURBT[a] (N = 138) | TURBT Alone (N = 132) |
|---|---|---|
| Treatment-emergent Adverse Events, n (%) | | |
| Any TEAE | 104 (75) | 63 (48) |
| Treatment discontinuation due to TEAE | 5 (3.6) | NA |
| Serious TEAEs | 12 (8.7) | 7 (5.3) |
| Treatment-related[b] serious TEAEs | 0 | 1 (0.8) |
| TEAEs ≥5% in Any Treatment Group | | |
| Dysuria | 42 (30) | 6 (4.5) |
| Micturition urgency | 25 (18) | 10 (7.6) |
| Nocturia | 25 (18) | 9 (6.8) |
| Pollakiuria | 22 (16) | 8 (6.1) |
| Flatulence | 13 (9.4) | 4 (3.0) |
| COVID-19 | 11 (8.0) | 8 (6.1) |
| Erectile dysfunction | 9 (6.5) | 4 (3.0) |
| Hematuria | 9 (6.5) | 6 (4.5) |
| Malaise | 8 (5.8) | 2 (1.5) |

[a]Patients randomized to initial treatment with UGN-102 were eligible to be treated with TURBT if NCR at 3 months with residual LG NMIBC.
[b]Relationship of TEAE to study treatment as assessed by the investigator.

Further analyses of data are provided in Tables 12-15 as follows.

TABLE 12

Summary of response rate at scheduled disease assessments (3-month CR analysis set).

| | | UGN-102 ± TURBT (N = 92) | | TURBT alone (N = 89) | |
|---|---|---|---|---|---|
| Visit | Response | n (%) | CRR (95% CI) | n (%) | CRR (95% CI) |
| Month 6 | Complete Response | 85 (92.4) | 92.4 (84.9, 96.9) | 64 (71.9) | 71.9 (61.4, 80.9) |
| | Recurrence | 5 (5.4) | | 14 (15.7) | |
| | Indeterminate | 0 | | 1 (1.1) | |

TABLE 12-continued

Summary of response rate at scheduled disease assessments (3-month CR analysis set).

| Visit | Response | UGN-102 ± TURBT (N = 92) | | TURBT alone (N = 89) | |
|---|---|---|---|---|---|
| | | n (%) | CRR (95% CI) | n (%) | CRR (95% CI) |
| Month 9 | Complete Response | 74 (80.4) | 80.4 (70.9, 88.0) | 56 (62.9) | 62.9 (52.0, 72.9) |
| | Recurrence | 9 (9.8) | | 5 (5.6) | |
| | Indeterminate | 0 | | 1 (1.1) | |
| Month 12 | Complete Response | 69 (75.0) | 75.0 (64.9, 83.4) | 51 (57.3) | 57.3 (46.4, 67.7) |
| | Recurrence | 4 (4.3) | | 5 (5.6) | |
| | Indeterminate | 0 | | 0 | |
| Month 15 | Complete Response | 66 (71.7) | 71.7 (61.4, 80.6) | 49 (55.1) | 55.1 (44.1, 65.6) |
| | Recurrence | 2 (2.2) | | 1 (1.1) | |
| | Indeterminate | 0 | | 1 (1.1) | |
| Month 18 | Complete Response | 32 (34.8) | 34.8 (25.1, 45.4) | 23 (25.8) | 25.8 (17.1, 36.2) |
| | Recurrence | 1 (1.1) | | 1 (1.1) | |
| | Indeterminate | 2 (2.2) | | 0 | |
| Month 21 | Complete Response | 7 (7.6) | 7.6 (3.1, 15.1) | 4 (4.5) | 4.5 (1.2, 11.1) |
| | Recurrence | 0 | | 0 | |
| | Indeterminate | 0 | | 0 | |

TABLE 13

Summary demographics/baseline data by TURBT Naïve v. >=1 Prior TURBT.

| | TURBT Naïve (N = 164) | | >=1 prior TURBT (N = 118) | |
|---|---|---|---|---|
| | UGN-102 ± TURBT (N = 87) | TURBTAlone (N = 77) | UGN-102 ± TURBT (N = 55) | TURBT Alone (N = 63) |
| Median age (range), years | 66 (23, 85) | 65 (29, 83) | 69 (35, 85) | 69 (47, 88) |
| Sex, n (%) | | | | |
| Male | 64 (73.6) | 51 (66.2) | 41 (74.5) | 42 (66.7) |
| Female | 23 (26.4) | 26 (33.8) | 14 (25.5) | 21 (33.3) |
| Age Group (Years), n (%) | | | | |
| <65 | 33 (37.9) | 38 (49.4) | 18 (32.7) | 25 (39.7) |
| >=65 | 54 (62.1) | 39 (50.6) | 37 (67.3) | 38 (60.3) |
| Age Group (Years), n (%) | | | | |
| <75 | 67 (77.0) | 66 (85.7) | 43 (78.2) | 44 (69.8) |
| >=75 | 20 (23.0) | 11 (14.3) | 12 (21.8) | 19 (30.2) |
| BMI (kg/m) category, n (%) | | | | |
| <30 (kg/m2) | 69 (79.3) | 50 (64.9) | 35 (63.6) | 46 (73.0) |
| >=30 (kg/m2) | 14 (16.1) | 19 (24.7) | 20 (36.4) | 16 (25.4) |
| Tumor Size (cm), n (%) | | | | |
| <=3 cm | 30 (34.5) | 33 (42.9) | 39 (70.9) | 40 (63.5) |
| >3 cm | 54 (62.1) | 42 (54.5) | 13 (23.6) | 17 (27.0) |
| Tumor Count, n (%) | | | | |
| Single | 37 (42.5) | 23 (29.9) | 17 (30.9) | 17 (27.0) |
| Multiple | 46 (52.9) | 53 (68.8) | 36 (65.5) | 41 (65.1) |
| Missing | 4 (4.6) | 1 (1.3) | 2 (3.6) | 5 (7.9) |
| Previous LG NMIBC Episodes within 1 Year, n (%) | | | | |
| Yes | 9 (10.3) | 5 (6.5) | 32 (58.2) | 35 (55.6) |
| No | 78 (89.7) | 72 (93.5) | 23 (41.8) | 28 (44.4) |
| Number of Previous LG NMIBC Episodes, n (%) | | | | |
| Yes | 2 (2.3) | 3 (3.9) | 52 (94.5) | 62 (98.4) |
| No | 85 (97.7) | 74 (96.1) | 3 (5.5) | 1 (1.6) |
| Previous LG NMIBC Episodes, n (%) | | | | |
| <=2 | 87 (100.0) | 77 (100.0) | 42 (76.4) | 46 (73.0) |
| >2 | 0 (0.0) | 0 (0.0) | 13 (23.6) | 17 (27.0) |

TABLE 13-continued

Summary demographics/baseline data by TURBT Naïve v. >=1 Prior TURBT.

| | TURBT Naïve (N = 164) | | >=1 prior TURBT (N = 118) | |
|---|---|---|---|---|
| | UGN-102 ± TURBT (N = 87) | TURBTAlone (N = 77) | UGN-102 ± TURBT (N = 55) | TURBT Alone (N = 63) |
| Prior TURBT, n (%) | | | | |
| Yes | 0 (0.0) | 3 (3.9) | 52 (94.5) | 61 (96.8) |
| No | 87 (100.0) | 74 (96.1) | 3 (5.5) | 2 (3.2) |
| Smoking History, n (%) | | | | |
| Non-Smoker | 39 (44.8) | 37 (48.1) | 24 (43.6) | 36 (57.1) |
| Smoker | 48 (55.2) | 40 (51.9) | 31 (56.4) | 27 (42.9) |

TABLE 14

Summary of complete response rate (CRR) by subgroup TURBT Naïve v. >=1 Prior TURBT at 3 months.

| | TURBT Naive (N = 164) | | | | >=1 TURBT (N = 118) | | | |
|---|---|---|---|---|---|---|---|---|
| | UGN-102 ± TURBT (N = 87) | | TURBT Alone (N = 77) | | UGN-102 ± TURBT (N = 55) | | TURBT Alone (N = 63) | |
| | n (%) | CRR (95% CI) | n (%) | CRR (95% CI) | n (%) | CRR (95% CI) | n (%) | CRR (95% CI) |
| Complete Response | 51 (58.6) | 58.6 (47.6, 69.1) | 54 (70.1) | 70.1 (58.6, 80.0) | 41 (74.5) | 74.5 (61.0, 85.3) | 35 (55.6) | 55.6 (42.5, 68.1) |
| Non-Complete Response | 36 (41.4) | | 23 (29.9) | | 14 (25.5) | | 28 (44.4) | |
| Residual disease | 19 (21.8) | | 5 (6.5) | | 7 (12.7) | | 17 (27.0) | |
| Progression to HG disease | 9 (10.3) | | 4 (5.2) | | 3 (5.5) | | 5 (7.9) | |
| Indeterminate | 1 (1.1) | | 0 | | 2 (3.6) | | 0 | |
| Missing | 7 (8.0) | | 14 (18.2) | | 2 (3.6) | | 6 (9.5) | |

TABLE 15

Summary of CRR by month by TURBT Naïve v. >=1 Prior TURBT (3-month CRR analysis set).

| | | TURBT Naïve (N = 105) | | | | >=1 prior TURBT (N = 76) | | | |
|---|---|---|---|---|---|---|---|---|---|
| | | UGN-102 ± TURBT (N = 51) | | TURBT Alone (N = 54) | | UGN-102 ± TURBT (N = 41) | | TURBT Alone (N = 35) | |
| Visit | Response | n (%) | CRR (95% CI) | n (%) | CRR (95% CI) | n (%) | CRR (95% CI) | n (%) | CRR (95% CI) |
| Month 6 | Complete Response | 49 (96.1) | 96.1 (86.5, 99.5) | 44 (81.5) | 81.5 (68.6, 90.7) | 36 (87.8) | 87.8 (73.8, 95.9) | 20 (57.1) | 57.1 (39.4, 73.7) |
| | Recurrence | 1 (2.0) | | 6 (11.1) | | 4 (9.8) | | 8 (22.9) | |
| | Indeterminate | 0 (0.0) | | 0 (0.0) | | 0 (0.0) | | 1 (2.9) | |
| Month 9 | Complete Response | 43 (84.3) | 84.3 (71.4, 93.0) | 40 (74.1) | 74.1 (60.3, 85.0) | 31 (75.6) | 75.6 (59.7, 87.6) | 16 (45.7) | 45.7 (28.8, 63.4) |
| | Recurrence | 5 (9.8) | | 3 (5.6) | | 4 (9.8) | | 2 (5.7) | |
| | Indeterminate | 0 (0.0) | | 1 (1.9) | | 0 (0.0) | | 0 (0.0) | |
| Month 12 | Complete Response | 42 (82.4) | 82.4 (69.1, 91.6) | 39 (72.2) | 72.2 (58.4, 83.5) | 27 (65.9) | 65.9 (49.4, 79.9) | 12 (34.3) | 34.3 (19.1, 52.2) |
| | Recurrence | 1 (2.0) | | 1 (1.9) | | 3 (7.3) | | 4 (11.4) | |
| Month 15 | Complete Response | 42 (82.4) | 82.4 (69.1, 91.6) | 38 (70.4) | 70.4 (56.4, 82.0) | 24 (58.5) | 58.5 (42.1, 73.7) | 11 (31.4) | 31.4 (16.9, 49.3) |
| | Recurrence | 0 (0.0) | | 0 (0.0) | | 2 (4.9) | | 1 (2.9) | |
| | Indeterminate | 0 (0.0) | | 1 (1.9) | | 0 (0.0) | | 0 (0.0) | |
| Month 18 | Complete Response | 2 (47.1) | 47.1 (32.9, 61.5) | 17 (31.5) | 31.5 (19.5, 45.6) | 8 (19.5) | 19.5 (8.8, 34.9) | 6 (17.1) | 17.1 (6.6, 33.6) |

TABLE 15-continued

Summary of CRR by month by TURBT Naïve v. >=1 Prior TURBT (3-month CRR analysis set).

| | | TURBT Naïve (N = 105) | | | | >=1 prior TURBT (N = 76) | | | |
|---|---|---|---|---|---|---|---|---|---|
| | | UGN-102 ± TURBT (N = 51) | | TURBT Alone (N = 54) | | UGN-102 ± TURBT (N = 41) | | TURBT Alone (N = 35) | |
| Visit | Response | n (%) | CRR (95% CI) | n (%) | CRR (95% CI) | n (%) | CRR (95% CI) | n (%) | CRR (95% CI) |
| | Recurrence | 1 (2.0) | | 0 (0.0) | | 0 (0.0) | | 1 (2.9) | |
| | Indeterminate | 1 (2.0) | | 0 (0.0) | | 1 (2.4) | | 0 (0.0) | |
| Month 21 | Complete Response | 4 (7.8) | 7.8 (2.2, 18.9) | 2 (3.7) | 3.7 (0.5, 12.7) | 3 (7.3) | 7.3 (1.5, 19.9) | 2 (5.7) | 5.7 (0.7, 19.2) |

Figure 7:
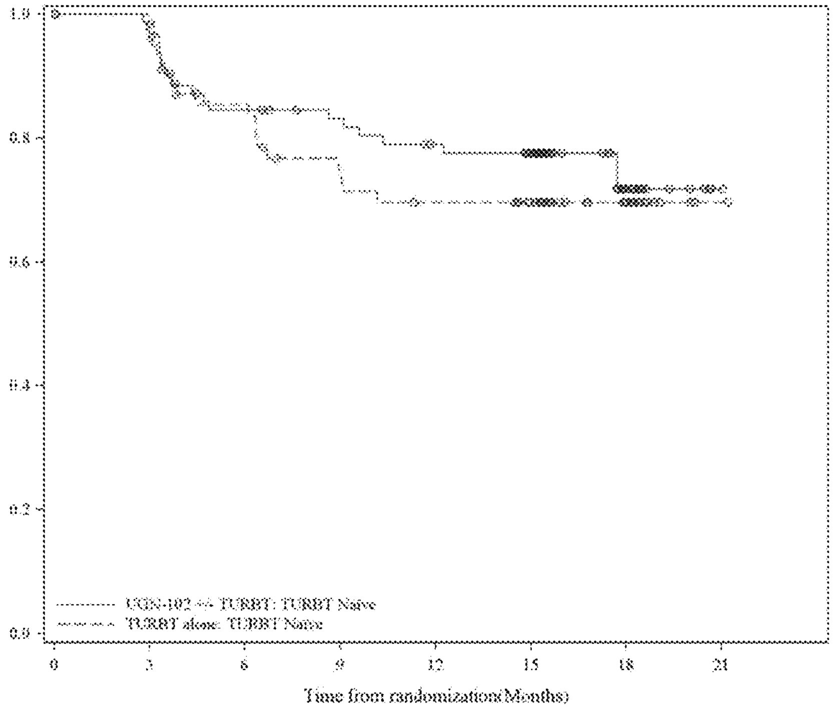
FIG. 7 shows a summary of disease-free survival (DFS) for the TURBT Naïve subgroup in the ATLAS study.

FIG. 7 shows a summary of disease-free survival (DFS) for the TURBT Naïve subgroup.

Figure 8:
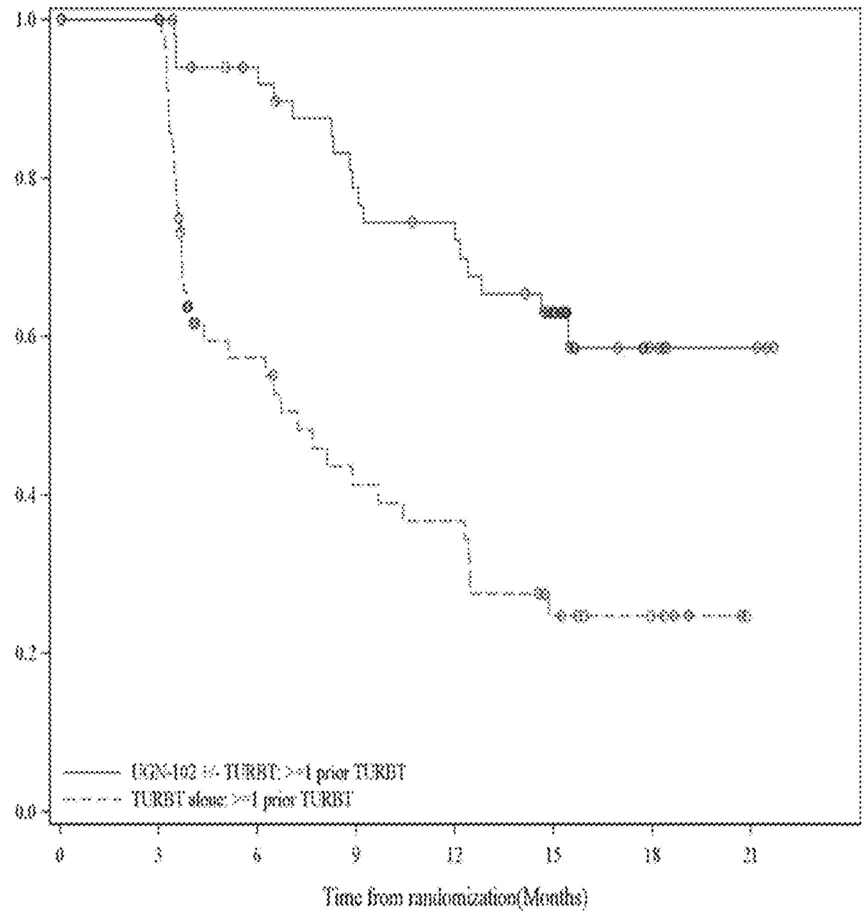
FIG. 8 shows a summary of disease-free survival (DFS) for the ≥1 TURBT subgroup in the ATLAS study.

FIG. 8 shows a summary of disease-free survival (DFS) for the ≥1 TURBT subgroup.

Figure 9:
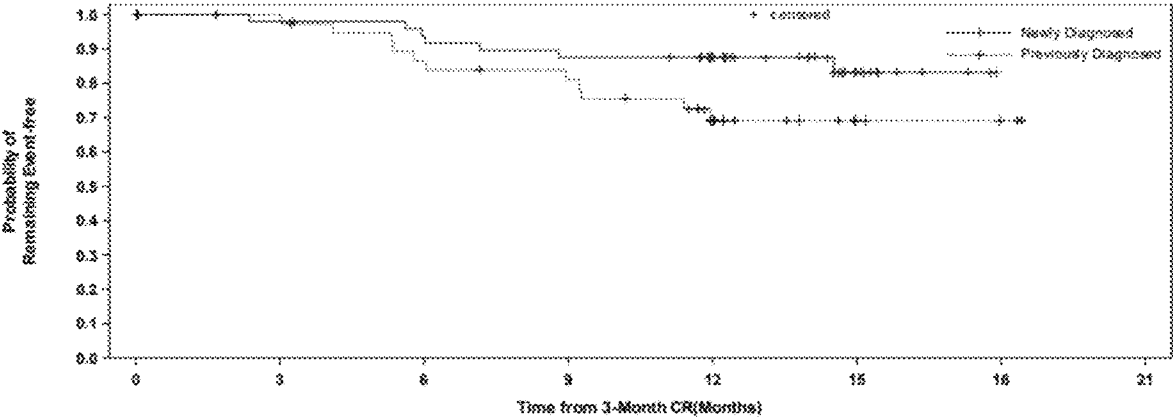
FIG. 9 shows probabilities of duration of response from 3-month CR for new and recurrent patients in the ATLAS study.
Figure 10:
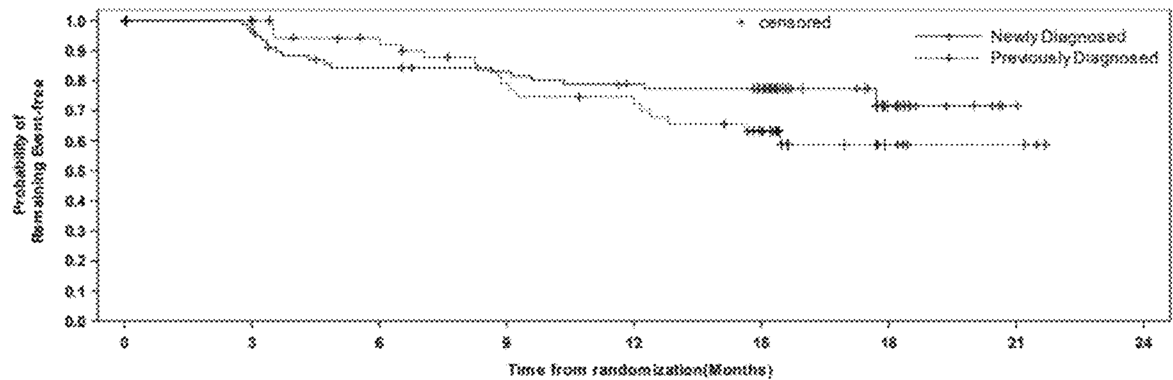
FIG. 10 shows probabilities of disease-free survival for new and recurrent patients in the ATLAS study.

Post-hoc analyses demonstrated new and recurrent LG IR NMIBC patients treated with UGN-102 alone achieved similar probabilities of duration of response (87.5% and 69.1% at 12 months from 3-month CR for new and recurrent patients, respectively) (see FIG. 9) and patients treated with UGN+/−TURBT achieved similar probabilities of disease-free survival (77.4% and 63.2% at 15 months from randomization for new and recurrent patients, respectively) (see FIG. 10).

TABLE 16

% Patients who received TURBT at 3 months.

| At the 3-Month Assessment | UGN-102 ± TURBT (N = 138) n (%) | TURBT Alone (N = 132) n (%) |
|---|---|---|
| TURBT | 24 (17.4%) | 18 (13.6%) |

Censoring in months 0-3: The number of patients by treatment arm who were censored prior to a DFS of 3.0 months were 11 patients in the UGN-102+/−TURBT arm and 20 patients in the TURBT alone arm.

Discussion

In the ATLAS trial, patients receiving induction treatment with UGN-102 achieved CR rates comparable to the surgical control group; however, treatment initially with UGN-102 with or without subsequent TURBT resulted in markedly improved probability of DFS compared with TURBT monotherapy as initial management. In addition, for patients achieving CR after initial treatment with UGN-102, the probability of maintaining response for ≥15 months post-treatment was greater than that for patients treated by TURBT monotherapy.

In particular, UGN-102 met its primary endpoint of disease-free survival, reducing risk of recurrence, progression, or death by 55%. UGN-102 also showed a 65% complete response rate at 3-months for patients who only received UGN-102, compared to a 64% complete response rate at 3-months for patients who only received a TURBT. While these rates were similar in both arms, DOR was superior in the UGN-102±TURBT arm. Analyses demonstrate that UGN-102±TURBT results in meaningful and similar DOR and DFS in patients with newly diagnosed and recurrent LG IR NMIBC.

Treatment with UGN-102±TURBT was associated with more TEAEs than TURBT monotherapy; however, patients in the drug treatment arm were queried weekly during induction therapy regarding adverse effects associated with treatment, whereas patients in the surgical arm were evaluated at monthly intervals via telephone contact up to the 3-month visit. This imbalance in evaluation may have introduced ascertainment bias into the study which in turn may underestimate TEAEs associated with TURBT. The most common TEAEs encountered with UGN-102 treatment were dysuria, micturition frequency, nocturia, and pollakiuria which are common side effects of local therapy for bladder cancer and often dissipate with time from the intervention.

The ATLAS study had limitations. First, in an effort to mimic contemporary treatment of LG NMIBC, patients randomized to TURBT monotherapy did not receive adjuvant intravesical therapy (despite current guidelines) which may have resulted in bias for the UGN-102±TURBT treatment group. Second, residual LG disease at the 3-month assessment was counted as a DFS event in the TURBT alone arm but not in the UGN-102 TURBT arm. Finally, while planned as a test of UGN-102 superiority to TURBT with a goal of enrolling 632 patients, the trial was closed to new enrollment at the request of the sponsor after 282 patients were randomized. Patients were treated and followed, and data was collected; however, the study reflects both the enrollment of a smaller cohort of patients than would have been required to satisfy the original statistical analysis plan and what was likely an excessively conservative estimate of the therapeutic benefit of UGN-102. The sponsor subsequently initiated another phase 3 trial (ENVISION, NCT05243550), an open-label, single-arm study of the safety and efficacy of UGN-102 in the treatment of recurrent IR NMIBC.

Conclusions

Treatment with UGN-102±TURBT resulted in improved probability of DFS and favorable DOR in patients with LG IR NMIBC compared to TURBT monotherapy in this study. Although treatment with UGN-102±TURBT was associated with more frequent TEAEs, there were no serious treatment-related TEAEs in the UGN-102 cohort. Primary chemoablation with UGN-102 provides a promising minimally invasive, non-surgical alternative to TURBT for initial treatment of patients with new or recurrent LG IR NMIBC that can be administered in an outpatient setting.

Phase 3 Single-Arm Study of UGN-102 for Treatment of Low Grade Intermediate Risk Non-Muscle-Invasive Bladder Cancer (ENVISION)

Study Design and Population

The Phase 3 ENVISION trial is a single-arm, multinational, multicenter study evaluating the efficacy and safety of UGN-102 (mitomycin) for intravesical solution as primary chemoablative therapy in patients with low-grade, intermediate-risk NMIBC. The Phase 3 ENVISION trial completed target enrollment with approximately 240 patients across 56 sites. More details about the Phase 3 ENVISION trial can be found at www.clinicaltrials.gov (NCT05243550).

Procedures

Eligible study participants received six once-weekly intravesical instillations of UGN-102.

All patients returned to the clinic approximately 3 months after the first instillation for determination of response to treatment. Assessment of response was based on visual observation (white light cystoscopy), histopathology of any remaining or new lesions by central pathology lab (if applicable), and interpretation of urine cytology by central pathology lab.

Patients confirmed to have a complete response (CR) at the 3-month Visit, defined as having no detectable disease (NDD) in the bladder, entered the Follow-up Period of the study. Patients confirmed to have a non-complete response (NCR) underwent Investigator designated standard of care (SOC) treatment of remaining lesions and then enter the Follow-up Period of the study.

During the Follow-up Period, patients will return to the clinic every 3 months for up to 24 months (i.e., 27 months after the first instillation) for evaluation of response. Patients who remain disease free at the 27-month Visit will continue to return to the clinic every 6 months for up to 36 months (i.e., 63 months after the first instillation) or until disease recurrence, disease progression, death, or the study is closed by the Sponsor, whichever occurs first.

Patients confirmed to have a disease recurrence during the Follow-up Period or a disease progression at the 3-month Visit or during the Follow-up Period will undergo Investigator designated SOC treatment and have a separate End of Study (EOS) Visit performed. The timing of the EOS Visit will be approximately 3 months after SOC treatment of disease recurrence or progression.

Outcomes

The primary endpoint evaluated the complete response rate at the 3-month assessment after the first instillation. The key secondary endpoints will evaluate duration of response (DOR), defined as time from first documented CR until the earliest date of recurrence, progression, or death; durable complete response (DCR) rate at scheduled disease assessment time points, defined as the proportion of patients who achieved CR at the 3-month Visit and maintained CR (i.e., no detectable disease) up to that particular follow-up disease assessment; and disease-free survival (DFS), defined as the time from first dose to the earliest date of recurrence or progression or death due to any cause, whichever occurred first. Incidence of treatment-emergent adverse events (TEAEs), serious TEAEs, TEAEs of special interest, and abnormal clinical laboratory test results (hematology, serum chemistry, and urinalysis) were summarized.

Results and Discussion

The most common treatment-emergent adverse events (TEAEs) in the ENVISION trial were dysuria, hematuria, urinary tract infection, pollakiuria, fatigue, and urinary retention. TEAEs were typically mild-to-moderate in severity. The ENVISION trial demonstrated a similar safety profile to that observed in other studies of UGN-102.

TABLE 17

Incidence of treatment related serious TEAEs (safety analysis set).

| Preferred Term | UGN-102 (N = 240) n (%) |
|---|---|
| Patients with Any Treatment Related Serious TEAE | 2 (0.8) |
| Urethral stenosis | 1 (0.4) |
| Urinary retention | 1 (0.4) |

TABLE 18

Incidence of deaths (safety analysis set).

| | UGN-102 (N = 240) n (%) |
|---|---|
| Total deaths anytime after first installation | 3 (1.3) |
| Death | 1 (0.4) |
| Pneumonia | 1 (0.4) |
| Cardiac failure | 1 (0.4) |

TABLE 19

Incidence of serious TEAEs (safety analysis set).

| Preferred Term | UGN-102 (N = 240) n (%) |
|---|---|
| Patients with Any Serious TEAE | 29 (12.1) |
| Atrial fibrillation | 2 (0.8) |
| Angina pectoris | 1 (0.4) |
| Antrioventricular block second degree | 1 (0.4) |
| Cardiac failure | 1 (0.4) |
| Cardiac failure acute | 1 (0.4) |
| Cardiac failure congestive | 1 (0.4) |
| Sinus node dysfunction | 1 (0.4) |
| COVID-19 | 2 (0.8) |
| Fournier's gangrene | 1 (0.4) |
| Pneumonia | 1 (0.4) |
| Urosepsis | 1 (0.4) |
| Carotid artery disease | 1 (0.4) |
| Carpal tunnel syndrome | 1 (0.4) |
| Cerebrovascular accident | 1 (0.4) |
| Transient ischaemic attack | 1 (0.4) |
| Adenocarcinoma pancreas | 1 (0.4) |
| Lip and/or oral cavity cancer | 1 (0.4) |
| Lung cancer metastatic | 1 (0.4) |
| Urinary retention | 2 (0.8) |
| Urethral stenosis | 1 (0.4) |
| Chronic obstructive pulmonary disease | 1 (0.4) |
| Dyspnoea | 1 (0.4) |
| Pulmonary embolism | 1 (0.4) |
| Haemorrhoids | 1 (0.4) |
| Incarcerated inguinal hernia | 1 (0.4) |
| Nausea | 1 (0.4) |
| Gallbladder polyp | 1 (0.4) |
| Jaundice cholestatic | 1 (0.4) |
| Acetabulum fracture | 1 (0.4) |
| Femur fracture | 1 (0.4) |

TABLE 19-continued

| Incidence of serious TEAEs (safety analysis set). | |
|---|---|
| Preferred Term | UGN-102 (N = 240) n (%) |
| Glaucoma | 1 (0.4) |
| Death | 1 (0.4) |
| Blood creatinine increased | 1 (0.4) |
| Hyponatremia | 1 (0.4) |
| Intervertebral disc protrusion | 1 (0.4) |
| Hypertensive crisis | 1 (0.4) |

TABLE 20

| AEs generally mild to moderate in severity. | |
|---|---|
| | (N = 240) n (% incidence) |
| Any adverse events | 140 (58.3) |
| Any serious adverse events | 30 (12.5) |
| Any TEAEs | 137 (57.1) |
| Any grade >=3 TEAEs | 33 (13.8) |
| Any treatment or procedure related TEAEs | 97 (40.4) |
| Any treatment related TEAEs | 81 (33.8) |
| Any procedure related TEAEs | 64 (26.7) |
| Any TEAEs leading to treatment discontinuation | 7 (2.9) |
| Any TEAEs leading to study discontinuation | 6 (2.5) |
| Any serious TEAEs | 29 (12.1) |
| Any treatment or procedure related serious TEAEs | 4 (1.7) |
| Any treatment related serious TEAEs* | 2 (0.8) |
| Any procedure related serious TEAEs | 3 (1.3) |
| Any TEAEs leading to death** | 3 (1.3) |
| Any TEAEs of special interest | 100 (41.7) |

*urethral stenosis and urinary retention (both resolved)
**unrelated to treatment - cardiac event, pneumonia, undisclosed The ENVISION trial met its primary endpoint by demonstrating a 76.700 rate of complete response at 3-months following the initial treatment. See Table 21.

TABLE 21

| Complete response rate at 3 months. | | |
|---|---|---|
| | n (%) | CRR (95% CI) |
| Complete response | 184 (76.7) | 76.7 (70.8, 81.9) |
| Non-complete response | 56 (23.3) | |
| Residual disease | 35 (14.6) | |
| Progression to HG disease | 7 (2.9) | |
| Indeterminate | 9 (3.8) | |
| Missing | 5 (2.1) | |

An 82.3% (95% CI, 75.9%, 87.1%) 12-month duration of response (DOR) by Kaplan-Meier estimate (n=108) was achieved in patients who achieved complete response (CR) at three months after the first instillation of UGN-102 (mitomycin). In addition to the 12-month data, the DOR Kaplan-Meier estimates at 15 (n=43) and 18 (n=9) months were both 80.9% (950% CI, 73.9%, 86.20%). See Table 22.

TABLE 22

| Duration of response (DOR) has potential to break of recurrence (N = 191). | |
|---|---|
| | Number (%) of patients with events 33 (17.3) Median (months) estimate NE (NE, NE)* |
| KM estimates at: | |
| 3 months | 96.8% |
| 6 months | 91.9% |
| 9 months | 86.9% |
| 12 months | 82.3% (75.9%, 87.1%) |
| 15 months | 80.9% (73.9%, 86.2%) |
| 18 months | 80.9% (73.9%, 86.2%) |

*NE = not estimable due to patients remaining in CR

Figure 11:
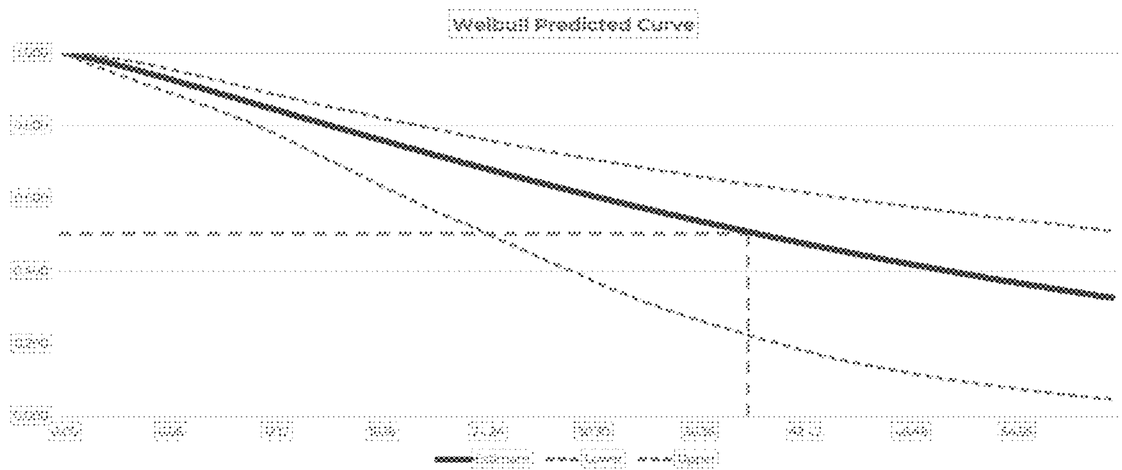
FIG. 11 shows the predicted median duration of response (DOR) for the ENVISION study.

A predicted median duration of response (DOR) is 40.0 months as shown in FIG. 11.

I claim:

1. A method of increasing probability of maintaining an achieved complete response for at least 15 months post-treatment initiation comprising the step of:

administering to a patient in need thereof nonsurgical primary chemoablation with a thermally gelling pharmaceutical composition comprising 75 mg of mitomycin once weekly for six weeks, wherein the patient in need thereof has recurrent low-grade intermediate-risk non- muscle-invasive bladder cancer (NMIBC), wherein the patient in need thereof had a previous episode of low-grade NMIBC that was treated with transurethral resection of bladder cancer (TURBT), and wherein the thermally gelling pharmaceutical composition was prepared by mixing a composition comprising mitomycin together with a thermoreversible hydrogel comprising about 27% (w/w) Poloxamer 407 and about 0.18% (w/w) hydroxypropylmethylcellulose based on a total weight of the thermoreversible hydrogel.

2. The method according to claim 1, wherein the recurrent low-grade intermediate-risk NMIBC is diagnosed using cold cup biopsy.

3. The method according to claim 1, wherein the previous episode of low-grade NMIBC that was treated with TURBT occurred within one year of the administering step.

4. The method according to claim 2, wherein the previous episode of low-grade NMIBC that was treated with TURBT occurred within one year of the administering step.

* * * * *